United States Patent
Senda et al.

(10) Patent No.: US 10,662,411 B2
(45) Date of Patent: May 26, 2020

(54) CULTURE METHOD FOR STABLE PROLIFERATION OF PLURIPOTENT STEM CELL WHILE MAINTAINING UNDIFFERENTIATED STATE

(71) Applicant: AJINOMOTO CO., INC., Tokyo (JP)

(72) Inventors: Sho Senda, Kawasaki (JP); Tomomi Yoshida, Kawasaki (JP); Satoru Okamoto, Kawasaki (JP); Yoko Kuriyama, Kawasaki (JP); Manabu Kitazawa, Kawasaki (JP); Ikue Harata, Kawasaki (JP); Nao Sugimoto, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/242,463

(22) Filed: Jan. 8, 2019

(65) Prior Publication Data
US 2019/0136202 A1 May 9, 2019

Related U.S. Application Data

(63) Continuation of application No. 14/813,374, filed on Jul. 30, 2015, which is a continuation of application No. PCT/JP2013/085263, filed on Dec. 27, 2013.

(30) Foreign Application Priority Data

Jan. 31, 2013 (JP) .................. 2013-016592

(51) Int. Cl.
| | | |
|---|---|---|
| C12N 5/00 | (2006.01) | |
| C12N 5/02 | (2006.01) | |
| C12N 5/074 | (2010.01) | |
| C12N 5/0735 | (2010.01) | |

(52) U.S. Cl.
CPC ......... *C12N 5/0696* (2013.01); *C12N 5/0043* (2013.01); *C12N 5/0606* (2013.01); *C12N 2500/36* (2013.01); *C12N 2500/46* (2013.01); *C12N 2500/84* (2013.01); *C12N 2533/90* (2013.01)

(58) Field of Classification Search
CPC .................................................. C12N 5/0696
USPC ....................................................... 435/325
See application file for complete search history.

(56) References Cited

U.S. PATENT DOCUMENTS

| | | |
|---|---|---|
| 7,923,245 B2 | 4/2011 | Furue et al. |
| 8,569,061 B2 | 10/2013 | Nistor |
| 8,877,493 B2 | 11/2014 | Sekiguchi et al. |
| 2007/0141036 A1 | 6/2007 | Gorrochategui Barrueta |
| 2008/0050817 A1 | 2/2008 | Furue et al. |
| 2010/0184221 A1 | 7/2010 | Yokoo et al. |
| 2011/0014701 A1 | 1/2011 | Ghosh |
| 2012/0220031 A1 | 8/2012 | Sekiguchi et al. |
| 2013/0309768 A1 | 11/2013 | Furue et al. |

FOREIGN PATENT DOCUMENTS

| | | |
|---|---|---|
| CN | 1431299 A | 7/2003 |
| CN | 101984048 A | 3/2011 |
| JP | 2006-325445 A | 12/2006 |
| JP | 2009-542247 A | 12/2009 |
| JP | 2011-505152 A | 2/2011 |
| WO | WO 92/13526 A1 | 8/1992 |
| WO | WO 03/029417 A2 | 4/2003 |
| WO | WO 2005/087915 A2 | 9/2005 |
| WO | WO 2006/047380 A2 | 5/2006 |
| WO | WO 2008/007082 A2 | 1/2008 |
| WO | WO 2008/018190 A1 | 2/2008 |
| WO | WO 2005/063968 A1 | 7/2008 |
| WO | WO 2011/043405 A1 | 4/2011 |
| WO | WO 2012/019122 A2 | 2/2012 |
| WO | WO 2012/104936 A1 | 8/2012 |

OTHER PUBLICATIONS

International Preliminary Report on Patentability dated Aug. 4, 2015 in PCT/JP2013/085263 (English Translation only).
"ES Saibo, iPS Saibo no Baiyo ni StemSure™ Series", Wako Jun'yaku Jiho, ISSN 2010, vol. 78, No. 4, 2 pages.
"StemSureR Series", Wako BioWindow, 2012, No. 12O, 2 pages.
Kazutoshi Takahashi, et al .• "Induction of Pluripotent Stem Cells from Mouse Embryonic and Adult Fibroblast Cultures by Defined Factors", Cell, 126, Aug. 25, 2006, pp. 663-676.
Takamichi Miyazaki, et al., "Laminin E8 fragments support efficient adhesion and expansion of dissociated human pluripotent stem cells", Nature Communications, 2012, 3:1236, 11 pages.
Guokai Chen, et al., "Chemically defined conditions for human iPS cell derivation and culture", Nature Methods, National Institutes of Health, 2011, 8, (5). pp. 424-429.
Stefan Frank, "Small Molecule-Assisted, Line-Independent Maintenance of Human Pluripotent Stem Cells in Defined Conditions", PLoS One, 2012, vol. 7, No. 7, e41958, 13 pages.
Extended European Search Report dated Jun. 20, 2016 in Patent Application No. 13873618.6.
Tao-Sheng Li, et al., "Physiological levels of reactive oxygen species are required to maintain genomic stability in stem cells" National Institute of Health Public Access, Author Manuscript, Stem Cells, XP 055279054, Jan. 2010, 16 Pages.
Veronika Akopian, et al., "Comparison of defined culture systems for feeder cell free propagation of human embryonic stem cells" In Vitro Cellular & Developmental Biology—Animal, vol. 46, No. 3-4, XP55269715, 2010, pp. 247-258.

(Continued)

*Primary Examiner* — Valarie E Bertoglio
(74) *Attorney, Agent, or Firm* — Oblon, McClelland, Maier & Neustadt, L.L.P.

(57) ABSTRACT

Cultivating a pluripotent stem cell in a medium comprising at least one member selected from the group consisting of ethanolamine, an ethanolamine analog, and a pharmaceutically acceptable salt thereof, and which is substantially free of β-mercaptoethanol or contains β-mercaptoethanol at a concentration of not more than 9 μM, and the like, is effective for the proliferation of a pluripotent stem cell while maintaining an undifferentiated state.

11 Claims, 7 Drawing Sheets

(56) References Cited

OTHER PUBLICATIONS

Lan Luo, et al., "Effects of antioxidants on the quality and genomic stability of induced pluripotent stem cells" Scientific Reports, vol. 4: 3779, XP055279121, 2014, 7 Pages.
Singaporean Search Report and Written Opinion, dated Nov. 15, 2016, in Singaporean Patent Application No. 11201505965T.
Written Opinion issued in the corresponding Singaporean Patent Application No. 11201505965T.
Breyer (Experimental Hematology, 2006, 34: 1596-1601).
Chen (1967, Jour. Biol. Chem., 242: 173-181).
Liu (2007, Biochemical Engineering Journal, 33: 1-9).
Lu (2006, PNAS, 103: 4577-5693).
Levenstein (Stem. Cells. Dec. 2008; 26(12): 3099-3107).
European Office Action (Communication pursuant to Article 94(3) EPC), dated Dec. 13, 2019, in European Patent Application No. 13873618.6.
Sigma Aldrich, Product Catalogue; Product No. A7223.

CULTURE METHOD FOR STABLE PROLIFERATION OF PLURIPOTENT STEM CELL WHILE MAINTAINING UNDIFFERENTIATED STATE

CROSS REFERENCES TO RELATED APPLICATIONS

This application is a continuation of U.S. patent application Ser. No. 14/813,374, filed on Jul. 30, 2015, which is a continuation of International Patent Application No. PCT/JP2013/085263, filed on Dec. 27, 2013, and claims priority to Japanese Patent Application No. 2013-016592, filed on Jan. 31, 2013, all of which are incorporated herein by reference in their entireties.

BACKGROUND OF THE INVENTION

Field of the Invention

The present invention relates to culture methods for the proliferation of pluripotent stem cells while maintaining an undifferentiated state, and particularly relates to a culture method for stable proliferation of human pluripotent stem cells under serum-free, feeder-free conditions and under single seeding conditions while maintaining an undifferentiated state and the like.

Discussion of the Background

Pluripotent stem cells such as ES (Embryonic stem) cells, iPS (induced pluripotent stem) cells and the like are expected to be usable for regenerative medicine and the like in view of the superior proliferativity and pluripotency. In particular, iPS cells are considered a highly superior material for regenerative medicine, since production and obtainment are relatively easy, there are few ethical restrictions for production, and further, from the aspect of rejection in transplantation.

These pluripotent stem cells have conventionally been cultured by co-culture with a carrying cell (hereinafter a feeder cell) such as a fibroblast and the like in a medium containing serum. For example, in Cell, 2006, 126, 663-76, which is incorporated herein by reference in its entirety and which is the world-first report by Yamanaka et al. on the production of iPS cells, iPS cells were established and maintained and proliferated under conditions using a feeder cell and serum. These pluripotent stem cells proliferate while forming a colony where individual cells are clustered. When a colony is dissociated into single cells and used for seeding (hereinafter single cell-seeding), the cells become unstable. It is therefore a general practice to seed a colony maintained to have a certain size (hereinafter colony seeding). For example, Nature Communications, 2012, 3:1236, which is incorporated herein by reference in its entirety, discloses an example showing that the proliferation conditions of cells are prone to influence from culture environment in the case of single cell-seeding compared to colony seeding. In other words, single cell-seeding poses higher culture difficulty than colony seeding.

To perform feeder-free culture, it is necessary to coat the bottom of a culture vessel with a substrate or scaffolding material replacing a feeder cell. As the substrate, an extracellular matrix component is often used. JP-A-2011-78370, which is incorporated herein by reference in its entirety, discloses that use of an active fragment of laminin 511 as a substrate is preferable for the proliferation of human ES/iPS cell, and single cell-seeding is also possible.

WO 2012/019122 and Nature Methods, 2011, 8, 424-429, both of which are incorporated herein by reference in their entireties, disclose the composition of a serum-free medium for human pluripotent stem cells. This composition called E8 contains DMEM/F12 as a basal medium, and further contains some factors such as bFGF, insulin and the like. At present, it is considered the minimum composition for cultivating human pluripotent stem cells.

Ethanolamine is known to contribute to the promoted proliferation of mesenchymal stem cells when used as an additive in a medium. For example, patent document 3 patent document 3: JP-A-2006-325445, which is incorporated herein by reference in its entirety, discloses an example suggesting that ethanolamine promotes proliferation of mesenchymal stem cells.

In addition, JP-A-2009-542247, which is incorporated herein by reference in its entirety, describes a method of maintaining primate embryonic stem cells in a medium containing ethanolamine, 2-mercaptoethanol, a complex of oleic acid with fatty acid-free bovine albumin, heparin and the like, and the like, and WO 2005/063968, which is incorporated herein by reference in its entirety, describes a medium for culturing ES cells, which contains 2-mercaptoethanol, 2-ethanolamine, a complex of oleic acid with fatty acid-free bovine serum albumin and the like. U.S. Pat. No. 8,569,061, which is incorporated herein by reference in its entirety, discloses a medium for ES cells, which contains human albumin, ethanolamine, β-mercaptoethanol and the like.

The above-mentioned JP-A-2009-542247, WO 2005/063968, and U.S. Pat. No. 8,569,061 describe given amounts (10 μM, 10 μM, 100 μM, respectively) of 2-mercaptoethanol (R-mercaptoethanol) as an essential component of medium. In JP-A-2009-542247, oleic acid is added to bovine albumin after removal of fatty acid, such that the bovine albumin carries oleic acid, and 9.4 mg/g of oleic acid is added to albumin.

In the meantime, it has been reported heretofore that sulfated polysaccharides have an effect to protect growth factors from degradation, denaturation, inactivation and the like. For example, WO 92/13526, which is incorporated herein by reference in its entirety, discloses that carrageenan stabilizes bFGF, and describes in the Examples that a protecting agent containing sulfated polysaccharides such as heparin, dextran sulfate, carrageenan and the like protects bFGF from hydrolysis and heat denaturation. However, an effect provided by a combination of ethanolamine and sulfated polysaccharides is not disclosed. Moreover, the above-mentioned JP-A-2009-542247 discloses a medium integrally containing ethanolamine and heparin; however, a detailed effect of each of them has not been known to date.

SUMMARY OF THE INVENTION

The above-mentioned conventional culture methods pose various problems when practicing a regenerative medicine using a pluripotent stem cells, particularly at an industrial level. As a feeder cell, xenogenic cells such as mouse embryo-derived fibroblast and the like are generally used, and the problem of safety after transplantation has been pointed out. Also, from the aspects of cost and cell quality management, culture without using a feeder cell (hereinafter feeder-free culture) is preferable. As for serum, the problem of infection source, and concern about property difference between lots which causes inconsistent culture results have been pointed out. As for the colony seeding, the number of seeded cells cannot be adjusted rigorously, which makes it difficult to manage culture schedule, and produces personal variation in the culture results. To produce pluripotent stem cells for a regenerative medicine at an industrial level, the work needs to be performed by plural workers under the conditions where procedures and schedule are rigorously managed. Moreover, since β-mercaptoethanol, which is generally added to a medium for pluripotent stem cell, is designated as toxin, it is preferable to not add the same to a medium or reduce the amount thereof to be added as much as possible, considering the complicated handling and the like. The influence of its amount to be added on the culture of pluripotent stem cells has not been clarified in detail yet.

From the foregoing, there is a demand for the development of a culture method, which adopts serum-free, feeder-free and single cell-seeding of pluripotent stem cells, and is different from conventional culture methods. In addition, cost is a major issue at an industrial level. Therefore, a mere success in the performance of serum-free, feeder-free and single cell-seeding culture is not sufficient, and such culture affording the largest possible number of cells per unit time, namely, culture with superior proliferation efficiency, is desirable.

The present inventors tried serum-free, feeder-free and single cell-seeding culture by a conventional culture method using the active fragment of laminin 511 described in JP-A-2011-78370 as a substrate and a medium having the E8 composition. However, they could not perform stable maintenance culture for a long term. It is necessary to elucidate and overcome the cause of such instability in culture, and further improve the proliferative ability.

It is therefore an object of the present invention to provide a means for proliferating pluripotent stem cells while maintaining an undifferentiated state. A further object of the present invention is to provide a means for stably and highly efficiently proliferating pluripotent stem cells while maintaining an undifferentiated state, in serum-free, feeder-free and single cell-seeding culture.

Means of Solving the Problems

The present inventors have conducted intensive studies in an attempt to solve the aforementioned problems and found that a feeder cell releases ethanolamine, and ethanolamine promotes the proliferation of pluripotent stem cells. They have also found that E8 causes remarkable property degradation after thawing and preparation, which may possibly cause instability of culture using E8, and further found that albumin can suppress such property degradation. They have also found that albumin not only has a medium stabilizing effect but also has an action to potentiate the above-mentioned cell proliferation effect of ethanolamine. They have also found that sulfated saccharides have a proliferation promoting and medium stabilizing effect in the presence of ethanolamine. The present inventors further showed that the amounts of β-mercaptoethanol, and fatty acid carried by albumin influence proliferation of pluripotent stem cells while maintaining an undifferentiated state. The present inventors have conducted further studies based on these findings and completed the present invention.

Accordingly, the present invention is as described below.

(1) A culture method for a proliferation of a pluripotent stem cell while maintaining an undifferentiated state, comprising a step of cultivating the pluripotent stem cell in a medium added with at least one selected from the group consisting of ethanolamine, ethanolamine analogs and pharmaceutically acceptable salts thereof, and substantially free of β-mercaptoethanol or containing β-mercaptoethanol at a concentration of not more than 9 μM.

(2) The method of (1), wherein the concentration of at least one selected from the group consisting of ethanolamine, ethanolamine analogs and pharmaceutically acceptable salts thereof in the medium is 1 μM-1000 μM.

(3) The method of (1), wherein the concentration of at least one selected from the group consisting of ethanolamine, ethanolamine analogs and pharmaceutically acceptable salts thereof in the medium is 5 μM-200 μM.

(4) The method of any of (1)-(3), wherein the ethanolamine analog is a compound represented by the following formula

wherein
X is $R^1$—$N(R^2)$—[$R^1$ and $R^2$ are the same or different and each is a hydrogen atom or an amino-protecting group] or $R^3$—CH=N—[$R^3$—CH is H—CH or a Shiff base type amino-protecting group]; and
Y is —P(=O)(OH)—O—$R^4$ [$R^4$ is —$CH_2$—CH(O—$R^5$)—$CH_2$—O—$R^6$ ($R^5$ and $R^6$ are the same or different and each is an acyl group having 2-30 carbon atoms or a hydrogen atom) or a hydrogen atom], a hydrogen atom or a hydroxy-protecting group.

(5) The method of (4), wherein $R^1$ and $R^2$ are the same or different and each is a hydrogen atom, a halogen atom, a hydroxy group, an aryl group, an acyl group having 2-30 carbon atoms, an alkyl group having 1-6 carbon atoms, an alkoxyl group having 1-6 carbon atoms, a hydroxyalkyl group having 1-6 carbon atoms, a haloalkyl group having 1-6 carbon atoms, a haloalkoxyl group having 1-6 carbon atoms or a halohydroxyalkyl group having 1-6 carbon atoms, and
$R^3$ is a hydrogen atom, a halogen atom, a hydroxy group, an aryl group, an acyl group having 2-30 carbon atoms, an alkyl group having 1-6 carbon atoms, an alkoxyl group having 1-6 carbon atoms, a hydroxyalkyl group having 1-6 carbon atoms, a haloalkyl group having 1-6 carbon atoms, a haloalkoxyl group having 1-6 carbon atoms or a halohydroxyalkyl group having 1-6 carbon atoms.

(6) The method of any of (1)-(3), wherein the ethanolamine analog is one or plural selected from the group consisting of phosphoethanolamine, monomethylethanolamine, dimethylethanolamine, N-acylphosphatidylethanolamine, phosphatidylethanolamine, and lysophosphatidylethanolamine.

(7) The method of any of (1)-(6), wherein the medium is further added with albumin.

(8) The method of (7), wherein the concentration of the albumin in the medium is 0.1 g/l-20 g/l.

(9) The method of (7), wherein the concentration of the albumin in the medium is 1 g/l-8 g/l.

(10) The method of any of (7)-(9), wherein the albumin is obtained from plasma of an animal (including human) or by gene recombination technology.

(11) The method of any of (7)-(10), wherein the amount of fatty acid carried by the albumin in the medium is not more than 9 mg/g.

(12) The method of any of (7)-(10), wherein the amount of fatty acid carried by the albumin in the medium is not more than 2.2 mg/g.

(13) The method of any of (1)-(12), wherein the medium is further added with sulfated saccharide and/or a pharmaceutically acceptable salt thereof.

(14) The method of (13), wherein the concentration of the sulfated saccharide and/or a pharmaceutically acceptable salt thereof in the medium is 1-1000 ng/ml.

(15) The method of (13) or (14), wherein the sulfated saccharide or a pharmaceutically acceptable salt thereof is dextran sulfate Na having an average molecular weight of 2,500-7,500.

(16) A culture method for a proliferation of a pluripotent stem cell while maintaining an undifferentiated state, comprising a step of cultivating the pluripotent stem cell in a medium added with at least one selected from the group consisting of ethanolamine, ethanolamine analogs and pharmaceutically acceptable salts thereof, and added with sulfated saccharide and/or a pharmaceutically acceptable salt thereof.

(17) The method of (16), wherein the concentration of the sulfated saccharide and/or a pharmaceutically acceptable salt thereof in the medium is 1-1000 ng/ml.

(18) The method of (16) or (17), wherein the sulfated saccharide or a pharmaceutically acceptable salt thereof is dextran sulfate Na having an average molecular weight of 2,500-7,500.

(19) The method of any of (16)-(18), wherein the medium is further added with albumin.

(20) The method of (19), wherein the concentration of the albumin in the medium is 0.1 g/l-20 g/l.

(21) The method of (19), wherein the concentration of the albumin in the medium is 1 g/l-8 g/l.

(22) The method of any of (19)-(21), wherein the albumin is obtained from plasma of an animal (including human) or by gene recombination technology.

(23) The method of any of (1)-(22), wherein the culture is performed in the absence of a feeder cell.

(24) The method of (23), wherein the culture is performed by using an extracellular matrix or an active fragment thereof, or an artificial product mimicking the function thereof.

(25) The method of (23), wherein the culture is performed by using laminin 511 or an active fragment thereof or matrigel.

(26) The method of any of (1)-(25), wherein the culture is performed by single cell-seeding.

(27) The method of any of (1)-(26), wherein the culture is performed under serum-free conditions.

(28) The method of any of (1)-(27), wherein the medium is substantially free of a component derived from an animal other than human.

(29) The method of any of (1)-(28), wherein the pluripotent stem cell is an embryonic stem cell (ES cell) or induced pluripotent stem cell (iPS cell).

(30) The method of any of (1)-(29), wherein the pluripotent stem cell is derived from primates.

(31) The method of any of (1)-(30), wherein the pluripotent stem cell is human iPS cell.

(32) A preservation stabilizing method for a medium for a proliferation of a pluripotent stem cell, comprising adding at least one selected from the group consisting of ethanolamine, ethanolamine analogs and pharmaceutically acceptable salts thereof, and adding sulfated saccharide and/or a pharmaceutically acceptable salt thereof.

(33) The method of (32), wherein the final concentration of the sulfated saccharide and/or a pharmaceutically acceptable salt thereof in use is 1-1000 ng/ml.

(34) The method of (32) or (33), further comprising adding albumin.

(35) The method of (34), wherein the final concentration of the albumin in use is 0.1 g/l-20 g/l.

(36) The method of [34], wherein the final concentration of the albumin in use is 1 g/l-8 g/l.

(37) The method of any of (34)-(36), wherein the albumin is obtained from plasma of an animal (including human) or by gene recombination technology.

(38) The method of any of (34)-(37), wherein the amount of fatty acid carried by the albumin is not more than 9 mg/g.

(39) The method of any of (34)-(37), wherein the amount of fatty acid carried by the albumin is not more than 2.2 mg/g.

(40) The method of any of (32)-(39), wherein the medium is substantially free of β-mercaptoethanol or contains β-mercaptoethanol at a final concentration of not more than 9 μM.

(41) The method of any of (32)-(40), wherein the medium is for a proliferation of a pluripotent stem cell while maintaining an undifferentiated state.

(42) A medium additive for a proliferation of a pluripotent stem cell while maintaining an undifferentiated state, comprising at least one selected from the group consisting of ethanolamine, ethanolamine analogs and pharmaceutically acceptable salts thereof, and substantially free of β-mercaptoethanol or containing β-mercaptoethanol at a concentration of not more than 9 μM when in use.

(43) The medium additive of (42), wherein the ethanolamine analog is a compound represented by the following formula

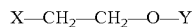

wherein
X is $R^1$—N($R^2$)—[$R^1$ and $R^2$ are the same or different and each is a hydrogen atom or an amino-protecting group] or $R^3$—CH=N—[$R^3$—CH is H—CH or a Shiff base type amino-protecting group]; and
Y is —P(=O)(OH)—O—$R^4$ [$R^4$ is —$CH_2$—CH(O—$R^5$)—$CH_2$—O—$R^6$ ($R^5$ and $R^6$ are the same or different and each is an acyl group having 2-30 carbon atoms or a hydrogen atom) or a hydrogen atom], a hydrogen atom or a hydroxy-protecting group.

(44) The medium additive of (43), wherein $R^1$ and $R^2$ are the same or different and each is a hydrogen atom, a halogen atom, a hydroxy group, an aryl group, an acyl group having 2-30 carbon atoms, an alkyl group having 1-6 carbon atoms, an alkoxyl group having 1-6 carbon atoms, a hydroxyalkyl group having 1-6 carbon atoms, a haloalkyl group having 1-6 carbon atoms, a haloalkoxyl group having 1-6 carbon atoms or a halohydroxyalkyl group having 1-6 carbon atoms, and
$R^3$ is a hydrogen atom, a halogen atom, a hydroxy group, an aryl group, an acyl group having 2-30 carbon atoms, an alkyl group having 1-6 carbon atoms, an alkoxyl group having 1-6 carbon atoms, a hydroxyalkyl group having 1-6 carbon atoms, a haloalkyl group having 1-6 carbon atoms, a haloalkoxyl group having 1-6 carbon atoms or a halohydroxyalkyl group having 1-6 carbon atoms.

(45) The medium additive of any of (42)-(44), wherein the ethanolamine analog is one or plural selected from the group consisting of phosphoethanolamine, monomethylethanolamine, dimethylethanolamine, N-acylphosphatidylethanolamine, phosphatidylethanolamine, and lysophosphatidylethanolamine.

(46) The medium additive of any of (42)-(45), further comprising albumin.

(47) The medium additive of (46), wherein the final concentration of the albumin in use is 0.1 g/l-20 g/l.

(48) The medium additive of (46), wherein the final concentration of the albumin in use is 1 g/l-8 g/l.

(49) The medium additive of any of (46)-(48), wherein the amount of fatty acid carried by the albumin is not more than 9 mg/g.

(50) The medium additive of any of (46)-(48), wherein the amount of fatty acid carried by the albumin is not more than 2.2 mg/g.

(51) The medium additive of any of (46)-(50), wherein the albumin is obtained from plasma of an animal (including human) or by gene recombination technology.

(52) The medium additive of any of (42)-(51), further comprising sulfated saccharide and/or a pharmaceutically acceptable salt thereof.

(53) The medium additive of (52), wherein the final concentration of the sulfated saccharide and/or a pharmaceutically acceptable salt thereof in use is 1-1000 ng/ml.

(54) The medium additive of (52) or (53), wherein the sulfated saccharide is at least one selected from the group consisting of sulfated monosaccharide, sulfated disaccharide, sulfated polysaccharide, sulfated sugar alcohol and sulfated cyclitol.

(55) The medium additive of any of (52)-(54), wherein the aforementioned sulfated saccharide or a pharmaceutically acceptable salt thereof is at least one selected from the group consisting of dextran sulfate Na, cellulose $SO_3Na$, xanthan gum $SO_3Na$, fucoidan, alginate $SO_3Na$, inulin $SO_3Na$, maltoheptaose $SO_3Na$, stachyose $SO_3Na$, maltotriose $SO_3Na$, multitol $SO_3Na$, sucrose8$SO_3K$, glucose $SO_3Na$, myo-6 inositol $SO_3K$, α-cyclodextrin $SO_3Na$, mannitol $SO_3Na$, xylitol $SO_3Na$ and erythritol $SO_3Na$.

(56) The medium additive of [55], wherein the aforementioned sulfated saccharide or a pharmaceutically acceptable salt thereof is at least one selected from the group consisting of dextran sulfate Na, fucoidan, maltoheptaose $SO_3Na$, maltotriose $SO_3Na$, multitol $SO_3Na$ and sucrose8$SO_3K$.

(57) The medium additive of any of (52)-(56), wherein the aforementioned sulfated saccharide or a pharmaceutically acceptable salt thereof is dextran sulfate Na having an average molecular weight of 2,500-7,500.

(58) The medium additive of any of (42)-(57), wherein the proliferation of a pluripotent stem cell while maintaining an undifferentiated state is performed under the conditions without using a feeder cell.

(59) The medium additive of (58), wherein the conditions without using a feeder cell do not include use of a feeder cell but include use of an extracellular matrix or an active fragment thereof, or an artificial product mimicking the function thereof.

(60) The medium additive of (58), wherein the conditions without using a feeder cell do not include use of a feeder cell but include use of laminin 511 or an active fragment thereof or matrigel.

(61) The medium additive of any of (42)-(60), wherein the proliferation of a pluripotent stem cell while maintaining an undifferentiated state is performed by single cell-seeding.

(62) The medium additive of any of (42)-(61), wherein the proliferation of a pluripotent stem cell while maintaining an undifferentiated state is performed under serum-free conditions.

(63) The medium additive of any of (42)-(62), comprising substantially free of a component derived from an animal other than human.

(64) The medium additive of any of (42)-(63), wherein the pluripotent stem cell is an embryonic stem cell (ES cell) or induced pluripotent stem cell (iPS cell).

(65) The medium additive of any of (42)-(64), wherein the pluripotent stem cell is derived from primates.

(66) The medium additive of any of (42)-(65), wherein the pluripotent stem cell is human iPS cell.

(67) A medium for proliferation of a pluripotent stem cell while maintaining an undifferentiated state, which comprises the medium additive of any of (42)-(66).

(68) A culture method for a proliferation of an induced pluripotent stem cell (iPS cell) while maintaining an undifferentiated state, comprising a step of cultivating the induced pluripotent stem cell (iPS cell) in a medium added with at least one selected from the group consisting of ethanolamine, ethanolamine analogs and pharmaceutically acceptable salts thereof.

(69) The method of (68), wherein the concentration of at least one selected from the group consisting of ethanolamine, ethanolamine analogs and pharmaceutically acceptable salts thereof in the medium is 1 μM-1000 μM.

(70) The method of (68), wherein the concentration of at least one selected from the group consisting of ethanolamine, ethanolamine analogs and pharmaceutically acceptable salts thereof in the medium is 5 μM-200 μM.

(71) The method of any of (68)-(70), wherein the ethanolamine analog is a compound represented by the following formula

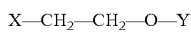

$$X—CH_2—CH_2—O—Y$$

wherein
X is $R^1$—N($R^2$)—[$R^1$ and $R^2$ are the same or different and each is a hydrogen atom or an amino-protecting group] or $R^3$—CH=N—[$R^3$—CH is H—CH or a Shiff base type amino-protecting group]; and
Y is —P(=O)(OH)—O—$R^4$ [$R^4$ is —$CH_2$—CH(O—$R^5$)—$CH_2$—O—$R^6$ ($R^5$ and $R^6$ are the same or different and each is an acyl group having 2-30 carbon atoms or a hydrogen atom) or a hydrogen atom], a hydrogen atom or a hydroxy-protecting group.

(72) The method of (71), wherein $R^1$ and $R^2$ are the same or different and each is a hydrogen atom, a halogen atom, a hydroxy group, an aryl group, an acyl group having 2-30 carbon atoms, an alkyl group having 1-6 carbon atoms, an alkoxyl group having 1-6 carbon atoms, a hydroxyalkyl group having 1-6 carbon atoms, a haloalkyl group having 1-6 carbon atoms, a haloalkoxyl group having 1-6 carbon atoms or a halohydroxyalkyl group having 1-6 carbon atoms, and
$R^3$ is a hydrogen atom, a halogen atom, a hydroxy group, an aryl group, an acyl group having 2-30 carbon atoms, an alkyl group having 1-6 carbon atoms, an alkoxyl group having 1-6 carbon atoms, a hydroxyalkyl group having 1-6 carbon atoms, a haloalkyl group having 1-6 carbon atoms, a haloalkoxyl group having 1-6 carbon atoms or a halohydroxyalkyl group having 1-6 carbon atoms.

(73) The method of any of (68)-(72), wherein the ethanolamine analog is one or plural selected from the group consisting of phosphoethanolamine, monomethylethanolamine, dimethylethanolamine, N-acylphosphatidylethanolamine, phosphatidylethanolamine, and lysophosphatidylethanolamine.

(74) The method of any of (68)-(73), wherein the medium is further added with albumin.

(75) The method of (74), wherein the concentration of the albumin in the medium is 0.1 g/l-20 g/l.

(76) The method of (74), wherein the concentration of the albumin in the medium is 1 g/l-8 g/l.

(77) The method of any of (74)-(76), wherein the albumin is obtained from plasma of an animal (including human) or by gene recombination technology.

(78) The method of any of (74)-(77), wherein the amount of fatty acid carried by the albumin in the medium is not more than 9 mg/g.

(79) The method of any of (74)-(77), wherein the amount of fatty acid carried by the albumin in the medium is not more than 2.2 mg/g.

(80) The method of any of (68)-(79), wherein the culture is performed in the absence of a feeder cell.

(81) The method of (80), wherein the culture is performed by using an extracellular matrix or an active fragment thereof, or an artificial product mimicking the function thereof.

(82) The method of (80), wherein the culture is performed by using laminin 511 or an active fragment thereof or matrigel.

(83) The method of any of (68)-(82), wherein the culture is performed by single cell-seeding.

(84) The method of any of (68)-(83), wherein the culture is performed under serum-free conditions.

(85) The method of any of (68)-(84), wherein the medium is substantially free of a component derived from an animal other than human.

(86) The method of any of (68)-(85), wherein the induced pluripotent stem cell is derived from primates.

(87) The method of any of (68)-(86), wherein the induced pluripotent stem cell is human iPS cell.

(88) A preservation stabilizing method for a medium for a proliferation of a pluripotent stem cell, comprising adding at least one selected from the group consisting of ethanolamine, ethanolamine analogs and pharmaceutically acceptable salts thereof.

(89) The method of (88), further comprising adding sulfated saccharide and/or a pharmaceutically acceptable salt thereof.

(90) The method of (89), wherein the final concentration of the sulfated saccharide and/or a pharmaceutically acceptable salt thereof in use is 1-1000 ng/ml.

(91) The method of any of (88)-(90), further comprising adding albumin.

(92) The method of (91), wherein the final concentration of the albumin in use is 0.1 g/l-20 g/l.

(93) The method of (91), wherein the final concentration of the albumin in use is 1 g/l-8 g/l.

(94) The method of any of (91)-(93), wherein the albumin is obtained from plasma of an animal (including human) or by gene recombination technology.

(95) The method of any of (91)-(94), wherein the amount of fatty acid carried by the albumin is not more than 9 mg/g.

(96) The method of any of (91)-(94), wherein the amount of fatty acid carried by the albumin is not more than 2.2 mg/g.

(97) The method of any of (88)-(96), wherein the medium is substantially free of β-mercaptoethanol or contains β-mercaptoethanol at a final concentration of not more than 9 μM.

(98) The method of any of (88)-(97), wherein the medium is for a proliferation of a pluripotent stem cell while maintaining an undifferentiated state.

(99) A medium additive for a proliferation of a pluripotent stem cell while maintaining an undifferentiated state, comprising at least one selected from the group consisting of ethanolamine, ethanolamine analogs and pharmaceutically acceptable salts thereof.

(100) The medium additive of [99], wherein the ethanolamine analog is a compound represented by the following formula

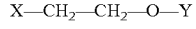

wherein

X is $R^1$—N($R^2$)—[$R^1$ and $R^2$ are the same or different and each is a hydrogen atom or an amino-protecting group] or $R^3$—CH=N—[$R^3$—CH is H—CH or a Shiff base type amino-protecting group]; and Y is —P(=O)(OH)—O—$R^4$ [$R^4$ is —$CH_2$—CH(O—$R^5$)—$CH_2$—O—$R^6$ ($R^5$ and $R^6$ are the same or different and each is an acyl group having 2-30 carbon atoms or a hydrogen atom) or a hydrogen atom], a hydrogen atom or a hydroxy-protecting group.

(101) The medium additive of (100), wherein $R^1$ and $R^2$ are the same or different and each is a hydrogen atom, a halogen atom, a hydroxy group, an aryl group, an acyl group having 2-30 carbon atoms, an alkyl group having 1-6 carbon atoms, an alkoxyl group having 1-6 carbon atoms, a hydroxyalkyl group having 1-6 carbon atoms, a haloalkyl group having 1-6 carbon atoms, a haloalkoxyl group having 1-6 carbon atoms or a halohydroxyalkyl group having 1-6 carbon atoms, and $R^3$ is a hydrogen atom, a halogen atom, a hydroxy group, an aryl group, an acyl group having 2-30 carbon atoms, an alkyl group having 1-6 carbon atoms, an alkoxyl group having 1-6 carbon atoms, a hydroxyalkyl group having 1-6 carbon atoms, a haloalkyl group having 1-6 carbon atoms, a haloalkoxyl group having 1-6 carbon atoms or a halohydroxyalkyl group having 1-6 carbon atoms.

(102) The medium additive of any of (99)-(101), wherein the ethanolamine analog is one or plural selected from the group consisting of phosphoethanolamine, monomethylethanolamine, dimethylethanolamine, N-acylphosphatidylethanolamine, phosphatidylethanolamine, and lysophosphatidylethanolamine.

(103) The medium additive of any of (99)-(102), further comprising albumin.

(104) The medium additive of (103), wherein the albumin is obtained from plasma of an animal (including human) or by gene recombination technology.

(105) The medium additive of any of (99)-(104), further comprising sulfated saccharide and/or a pharmaceutically acceptable salt thereof.

(106) The medium additive of (105), wherein the final concentration of the sulfated saccharide and/or a pharmaceutically acceptable salt thereof in use is 1-1000 ng/ml.

(107) The medium additive of (105) or (106), wherein the sulfated saccharide is at least one selected from the group consisting of sulfated monosaccharide, sulfated disaccharide, sulfated polysaccharide, sulfated sugar alcohol and sulfated cyclitol.

(108) The medium additive of any of (105)-(107), wherein the aforementioned sulfated saccharide or a pharmaceutically acceptable salt thereof is at least one selected from the group consisting of dextran sulfate Na, cellulose $SO_3Na$, xanthan gum $SO_3Na$, fucoidan, alginate $SO_3Na$, inulin $SO_3Na$, Maltoheptaose $SO_3Na$, stachyose $SO_3Na$, maltotriose $SO_3Na$, multitol $SO_3Na$, sucrose8$SO_3$K, glucose $SO_3Na$, myo-6 inositol $SO_3$K, α-cyclodextrin $SO_3Na$, mannitol $SO_3Na$, xylitol $SO_3Na$ and erythritol $SO_3Na$.

(109) The medium additive of (108), wherein the aforementioned sulfated saccharide or a pharmaceutically acceptable salt thereof is at least one selected from the group consisting of dextran sulfate Na, fucoidan, Maltoheptaose $SO_3Na$, maltotriose $SO_3Na$, multitol $SO_3Na$ and sucrose8$SO_3$K.

(110) The medium additive of any of (105)-(109), wherein the aforementioned sulfated saccharide or a pharmaceutically acceptable salt thereof is dextran sulfate Na having an average molecular weight of 2,500-7,500.

(111) The medium additive of any of (99)-(110), wherein the proliferation of a pluripotent stem cell while maintaining an undifferentiated state is performed under the conditions without using a feeder cell.

(112) The medium additive of (111), wherein the conditions without using a feeder cell do not include use of a feeder cell but include use of an extracellular matrix or an active fragment thereof, or an artificial product mimicking the function thereof.

(113) The medium additive of (111), wherein the conditions without using a feeder cell do not include use of a feeder cell but include use of laminin 511 or an active fragment thereof or matrigel.

(114) The medium additive of any of (99)-(113), wherein the proliferation of a pluripotent stem cell while maintaining an undifferentiated state is performed by single cell-seeding.

(115) The medium additive of any of (99)-(114), wherein the proliferation of a pluripotent stem cell while maintaining an undifferentiated state is performed under serum-free conditions.

(116) The medium additive of any of (99)-(115), comprising substantially free of a component derived from an animal other than human.

(117) The medium additive of any of (99)-(116), wherein the pluripotent stem cell is an embryonic stem cell (ES cell) or induced pluripotent stem cell (iPS cell).

(118) The medium additive of any of (99)-(117), wherein the pluripotent stem cell is derived from primates.

(119) The medium additive of any of (99)-(118), wherein the pluripotent stem cell is human iPS cell.

(120) A medium for proliferation of a pluripotent stem cell while maintaining an undifferentiated state, which comprises the medium additive of any of (99)-(119).

Effect of the Invention

According to the present invention, pluripotent stem cells can be stably and efficiently proliferated, and can be stably proliferated for a long term while maintaining an undifferentiated state even in serum-free, feeder-free and single cell-seeding culture.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
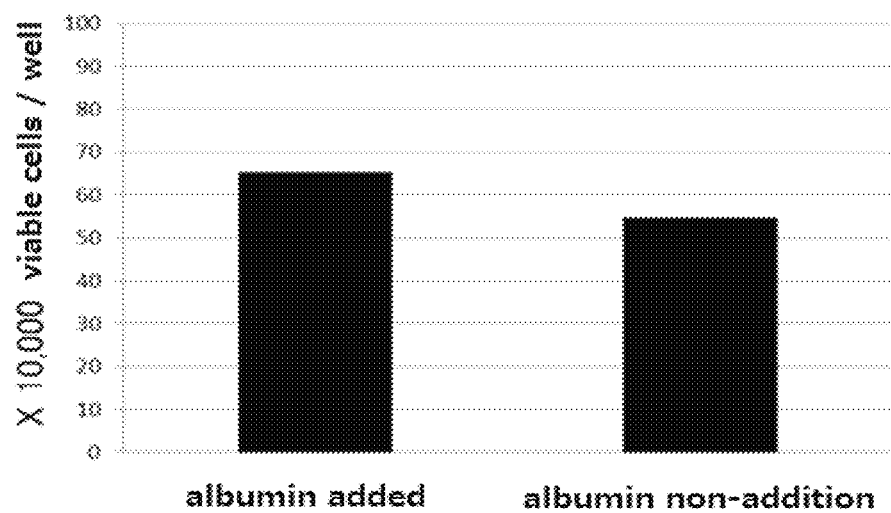
FIG. 1 shows a medium stabilizing effect by albumin under preservation conditions at 4° C.
Figure 1:
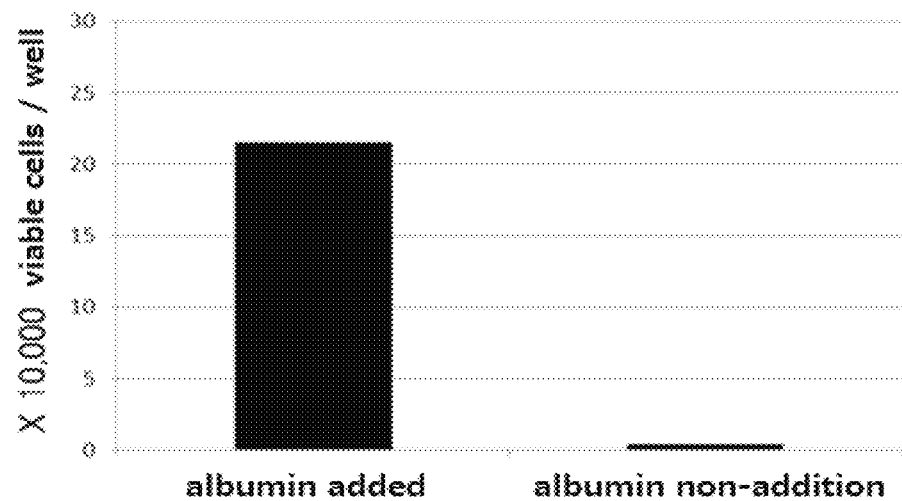

Culture method for proliferation of pluripotent stem cells while maintaining an undifferentiated state.

The present invention provides a culture method for the proliferation of a pluripotent stem cell while maintaining an undifferentiated state, comprising a step of cultivating a pluripotent stem cell in a medium added with at least one selected from the group consisting of ethanolamine, ethanolamine analogs and pharmaceutically acceptable salts thereof, and substantially free of β-mercaptoethanol or containing β-mercaptoethanol at a concentration of not more than 9 μM (hereinafter to be also referred to as the culture method of the present invention).

The present invention is based on the new finding that a feeder cell releases ethanolamine, and addition of ethanolamine can promote proliferation of pluripotent stem cells while maintaining an undifferentiated state even in feeder-free culture. As a feeder cell, xenogenic cells are generally used, and incidence of infection with a feeder cell-derived virus is also known. The present invention can solve these problems, and is extremely useful in the field of regenerative medicine.

Also, the present invention is based on the finding that pluripotent stem cells can be proliferated well while maintaining an undifferentiated state even when the concentration of β-mercaptoethanol in the medium is reduced. In the culture method of the present invention, the medium is preferably substantially or completely free of β-mercaptoethanol. Even when the medium contains β-mercaptoethanol, its concentration is preferably not more than 9 μM.

In the present specification, being "substantially free of β-mercaptoethanol" means that the content concentration of β-mercaptoethanol is below detection limit.

In the present invention, the "pluripotent stem cell" means an immature cell having self-renewal capacity and differentiation/proliferation capacity, which is capable of differentiating into any tissue or cell constituting living organisms. Examples of the pluripotent stem cell include embryonic stem cells (ES cells), embryonic germ cells (EG cells), induced pluripotent stem cells (iPS cells) and the like. A stem cell established by cultivating an early embryo generated by nuclear transplantation of the nucleus of a somatic cell is also included in the pluripotent stem cell (Nature, 385, 810 (1997); Science, 280, 1256 (1998); Nature Biotechnology, 17, 456 (1999); Nature, 394, 369 (1998); Nature Genetics, 22, 127 (1999); Proc. Natl. Acad. Sci. USA, 96, 14984 (1999); Nature Genetics, 24, 109 (2000), all of which are incorporated herein by reference in their entireties). The pluripotent stem cell in the present invention does not include a multipotent stem cell. The multipotent stem cell means a cell capable of differentiating into plural, though not all, types of tissues and cells and includes somatic stem cells such as mesenchymal stem cell and the like.

While the culture method of the present invention can be preferably used for any pluripotent stem cells, it is preferably used for proliferation of embryonic stem cells (ES cells) or induced pluripotent stem cells (iPS cells) while maintaining an undifferentiated state.

Also, the culture method of the present invention can be preferably used for pluripotent stem cells derived from any animals. The pluripotent stem cells cultured by using the medium of the present invention are, for example, pluripotent stem cells derived from rodents such as mouse, rat, hamster, guinea pig and the like, Lagomorpha such as rabbit and the like, Ungulata such as swine, bovine, goat, horse, sheep and the like, Carnivora such as dog, cat and the like, primates such as human, monkey, Macaca mulatta, marmoset, orangutan, chimpanzee and the like. Preferred are pluripotent stem cells derived from primates. When it is used for regenerative medicine, human iPS cells are preferable.

In the present invention, the "proliferation while maintaining an undifferentiated state" of pluripotent stem cells means that pluripotent stem cells can proliferate in an undifferentiated state while maintaining the pluripotency. That is, the culture method of the present invention can also be said to be a method of proliferating pluripotent stem cells in an undifferentiated state while maintaining pluripotency. Whether a pluripotent stem cell is maintained in an undifferentiated state is confirmed by alkaline phosphatase staining as shown in the below-mentioned Examples. Stained cells are evaluated as being maintained in an undifferentiated state.

The "ethanolamine" (also called 2-aminoethanol, monoethanolamine) used in the present invention may be isolated and purified from a natural product or a processed product thereof, or a synthesized product. Ethanolamine can be produced by reacting ethylene oxide and ammonia. Ethanolamine can also be isolated and purified from a natural product or a processed product thereof by known techniques such as solvent extraction, various chromatographys and the like. Ethanolamine may be a commercially available product and can be obtained from, for example, Sigma-Aldrich Co., Ltd. and the like.

Examples of the "ethanolamine analog" to be used in the present invention include a compound represented by the following formula

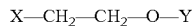

wherein
X is $R^1$—N($R^2$)—($R^1$ and $R^2$ are the same or different and each is a hydrogen atom or an amino-protecting group) or $R^3$—CH=N—($R^3$—CH is H—CH or a Shiff base type amino-protecting group); and
Y is —P(=O)(OH)—O—$R^4$ ($R^4$ is —CH$_2$—CH(O—$R^5$)—CH$_2$—O—$R^6$ ($R^5$ and $R^6$ are the same or different and each is an acyl group having 2 to 30 carbon atoms or a hydrogen atom) or a hydrogen atom, a hydrogen atom or a hydroxy-protecting group].

As for the "amino-protecting group", for example, books such as Green et al., Protective Groups in Organic Synthesis, 3rd Edition, 1999, John Wiley & Sons, Inc., which is incorporated herein by reference in its entirety, and the like can be referred to, and an appropriate protecting group can be selected, introduced and removed. Examples of the "amino-protecting group" include a halogen atom, a hydroxy group, an aryl group, an acyl group having 2 to 30 carbon atoms, an alkyl group having 1 to 6 carbon atoms, an alkoxyl group having 1 to 6 carbon atoms, a hydroxyalkyl group having 1 to 6 carbon atoms, a haloalkyl group having 1 to 6 carbon atoms, a haloalkoxyl group having 1 to 6 carbon atoms or a halohydroxyalkyl group having 1 to 6 carbon atoms. Furthermore, a leaving group that can be bound to an amino group for forming a prodrug can also be mentioned.

The "halogen atom" means a fluorine atom, a chlorine atom, a bromine atom, or an iodine atom.

Examples of the "aryl group" include phenyl, 1-naphthyl, 2-naphthyl and the like.

Examples of the "acyl group having 2 to 30 carbon atoms" include a saturated carboxylic acid acyl group and an unsaturated carboxylic acid acyl group. Examples of the saturated carboxylic acid acyl group include acetyl(ethanoyl), propanoyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, eicosanoyl, Henicosanoyl, Heneicosanoyl, docosanoyl, tricosanoyl, tetracosanoyl, pentacosanoyl, hexacosanoyl, heptacosanoyl, octacosanoyl, nonacosanoyl, triacontanoyl and the like. Examples of the unsaturated carboxylic acid acyl group include acryloyl, methacryloyl, crotonoyl, isocrotonoyl, butenoyl, butadienoyl, pentenoyl, hexenoyl, heptenoyl, octenoyl, nonenoyl, decenoyl, undecenoyl, dodecenoyl, tetradecenoyl, oleloyl, elaidinoyl, cyclopentanoyl, cyclohexanoyl, cycloheptanoyl, methylcyclopentanoyl, methylcyclohexanoyl, methylcycloheptanoyl, cyclopentenoyl, 2,4-cyclopentadienoyl, cyclohexenoyl, 2,4-cyclohexadienoyl, cycloheptenoyl, methylcyclopentenoyl, methylcyclohexenoyl, methylcycloheptenoyl and the like.

The "alkyl group having 1 to 6 carbon atoms" means a linear or branched alkyl group having 1 to 6 carbon atoms. Specific examples thereof include methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl and the like.

The "alkoxyl group having 1 to 6 carbon atoms" means a linear or branched alkoxyl group having 1 to 6 carbon atoms. Specific examples thereof include a methoxy group, an ethoxy group, a propoxy group, a butoxy group, a pentyloxy group, a hexyloxy group, a methoxymethoxy group, a methoxyethoxy group, a methoxypropoxy group, an ethoxyethoxy group, an ethoxypropoxy group and the like.

The "hydroxyalkyl group having 1 to 6 carbon atoms" means a linear or branched hydroxyalkyl group having 1 to 6 carbon atoms, wherein a part of the hydrogen atom in the alkyl group is substituted by a hydroxyl group. Specific examples thereof include a hydroxymethyl group, a 2-hydroxyethyl group, a 3-hydroxypropyl group, a 2-hydroxypropyl group, a 2-hydroxy-2-methylpropyl group, a 4-hydroxybutyl group, a 3-hydroxybutyl group, a 2-hydroxybutyl group and the like.

The "haloalkyl group having 1 to 6 carbon atoms" means a linear or branched haloalkyl group having 1 to 6 carbon atoms, wherein a part of the hydrogen atom in the alkyl group is substituted by a halogen atom, and the halogen atom is a fluorine atom, a chlorine atom, a bromine atom or an iodine atom. Specific examples thereof include a trifluoromethyl group, a chloromethyl group, a bromomethyl group, a dichloromethyl group, a difluoromethyl group, a trichloromethyl group, a 2-fluoroethyl group, a 2-chloroethyl group, a 2-bromoethyl group, a 1,1-difluoroethyl group, a 2,2,2-trifluoroethyl group, a 3-chloropropyl group, a 3-iodopropyl group and the like.

The "haloalkoxyl group having 1 to 6 carbon atoms" means a linear or branched haloalkoxyl group having 1 to 6 carbon atoms, wherein a part of the hydrogen atom in the alkoxy group is substituted by a halogen atom. Specific examples thereof include a trifluoromethoxy group, a pentafluoroethoxy group, a 2-chloroethoxy group, a 2,2,2-trifluoroethoxy group, a heptafluoro-n-propoxy group, a heptafluoro-i-propoxy group, a 1,1,1,3,3,3-hexafluoro-2-propoxy group, a 3-fluoro-n-propoxy group, a 1-chlorocyclopropoxy group, a 2-bromocyclopropoxy group, a 3,3,4,4,4-pentafluoro-2-butoxy group, a noanfluoro-n-butoxy group, a nonafluoro-2-butoxy group, a 5,5,5-trifluoro-n-pentyloxy group, a 4,4,5,5,5-pentafluoro-2-pentyloxy group, a 3-chloro-n-pentyloxy group, a 4-bromo-2-pentyloxy group, a 4-chlorobutyloxy group, a 2-iodo-n-propyloxy group and the like.

The "halohydroxyalkyl group having 1 to 6 carbon atoms" means a linear or branched halohydroxyalkyl group having 1 to 6 carbon atoms, wherein a part of the hydrogen atom in the hydroxylalkyl group is substituted by a halogen atom. Specific examples thereof include difluorohydroxymethyl, 1,1-difluoro-2-hydroxyethyl, 2,2-difluoro-2-hydroxyethyl, 1,1,2,2-tetrafluoro-2-hydroxyethyl group and the like.

The "forming a prodrug" in the "leaving group that can be bound to an amino group for forming a prodrug" means conversion of the target compound such that the compound which shows a small or no effect of the present invention shows the effect of the present invention upon removal of the leaving group in a medium and/or during culture. It means formation of a temporary bond between the amino group and the leaving group in the compound showing the effect of the present invention, which is removed in a medium and/or during culture.

The "leaving group that can be bound to an amino group for forming a prodrug" is not particularly limited as long as it is used in the field of synthetic organic chemistry. Examples thereof include a halogen atom (e.g., chlorine atom, bromine atom, iodine atom etc.), a sulfonyloxy group (e.g., methanesulfonyloxy group, trifluoromethanesulfonyloxy group, benzenesulfonyloxy group, p-toluenesulfonyloxy group etc.) and the like.

When $R^3$—CH is a Shiff base type amino-protecting group, $R^3$ is a halogen atom, a hydroxy group, an aryl group, an acyl group having 2 to 30 carbon atoms, an alkyl group having 1 to 6 carbon atoms, an alkoxyl group having 1 to 6 carbon atoms, a hydroxyalkyl group having 1 to 6 carbon atoms, a haloalkyl group having 1 to 6 carbon atoms, a haloalkoxyl group having 1-6 carbon atoms or a halohydroxyalkyl group having 1 to 6 carbon atoms.

While the "hydroxyl-protecting group" is not particularly limited as long as it is a hydroxyl-protecting group to be used in the field of synthetic organic chemistry, for example, an alkyl group having 1 to 6 carbon atoms (e.g., methyl, ethyl, propyl, isopropyl, butyl, tert-butyl), a phenyl group, a trityl group, an aralkyl group having 7 to 10 carbon atoms (e.g., benzyl, p-methoxybenzyl), a formyl group, an alkylcarbonyl group having 1 to 6 carbon atoms (e.g., acetyl, propionyl), a benzoyl group, an aralkyl-carbonyl group having 7 to 10 carbon atoms (e.g., benzylcarbonyl), methoxymethyl, ethoxyethyl, a 2-tetrahydropyranyl group, a 2-tetrahydrofuranyl group, substituted silyl group (e.g., trimethylsilyl, triethylsilyl, dimethylphenylsilyl, tert-butyldimethylsilyl, tert-butyldiethylsilyl), an alkenyl group having 2 to 6 carbon atoms (e.g., 1-allyl) and the like can be mentioned. Furthermore, a leaving group that can be bound to a hydroxy group for forming a prodrug can also be mentioned.

The "forming a prodrug" in the "leaving group that can be bound to a hydroxy group for forming a prodrug" means conversion of the target compound such that the compound which shows a small or no effect of the present invention shows the effect of the present invention upon removal of the leaving group in a medium and/or during culture. It means formation of a temporary bond between the hydroxy group and the leaving group in the compound showing the effect of the present invention, which is removed in a medium and/or during culture.

The "leaving group that can be bound to a hydroxy group for forming a prodrug" is not particularly limited as long as it is used in the field of synthetic organic chemistry. Examples thereof include a halogen atom (e.g., chlorine atom, bromine atom, iodine atom etc.), a sulfonyloxy group (e.g., methanesulfonyloxy group, trifluoromethanesulfonyloxy group, benzenesulfonyloxy group, p-toluenesulfonyloxy group etc.) and the like.

The ethanolamine analog is preferably one or plural selected from the group consisting of phosphoethanolamine (aka phosphoryl ethanolamine), monomethylethanolamine, dimethylethanolamine, N-acylphosphatidylethanolamine, phosphatidylethanolamine, and lysophosphatidylethanolamine.

The ethanolamine and/or ethanolamine analog to be used in the present invention may be in the form of a pharmaceutically acceptable salt. Examples of such salt when an acidic group such as a carboxyl group and the like is present in the compound include salts with alkali metals such as ammonium salt, sodium, potassium and the like, salts with alkaline earth metals such as calcium, magnesium and the like, salts with organic amines such as aluminum salt, zinc salt, triethylamine, morpholine, piperidine, dicyclohexylamine and the like, and salts with basic amino acids such as arginine, lysine and the like. Examples thereof when a basic group is present in the compound include salts with inorganic acids such as hydrochloric acid, sulfuric acid, phosphoric acid, nitric acid, hydrobromic acid and the like, salts with organic carboxylic acids such as acetic acid, trifluoroacetic acid, citric acid, benzoic acid, maleic acid, fumaric acid, tartaric acid, succinic acid, tannic acid, butyric acid, hibenzoic acid, pamoic acid, enanthic acid, decanoic acid, teoclic acid, salicylic acid, lactic acid, oxalic acid, mandelic acid, malic acid and the like, and salts with organic sulfonic acids such as methanesulfonic acid, benzenesulfonic acid, p-toluenesulfonic acid and the like. Particularly preferred is hydrochloride.

The final concentration (concentration when in use) of ethanolamine and/or ethanolamine analogs and pharmaceutically acceptable salts thereof in the medium can be determined to fall within any range as long as it can promote proliferation of pluripotent stem cells while maintaining an undifferentiated state under feeder-free conditions. While the final concentration can vary depending on the kind thereof, it is generally 1 μM to 1000 μM, preferably 5 μM to 200 μM, or 11 μM to 200 μM. When it is less than 1 μM, the effect of promoting proliferation of pluripotent stem cells while maintaining an undifferentiated state tends to be weak. When it exceeds 1000 μM, proliferation of pluripotent stem cells may sometimes be suppressed. The concentration of at least one selected from the group consisting of ethanolamine, ethanolamine analogs and pharmaceutically acceptable salts thereof in the medium is generally 1 μM to 1000 μM, preferably 5 μM to 200 μM, or 11 μM to 200 μM. When plural kinds are used, the total amount thereof is set to fall within the above-mentioned range. However, it can be increased or decreased as appropriate depending on the number of the kinds thereof.

In the present invention, that at least one selected from the group consisting of ethanolamine and/or ethanolamine analogs and pharmaceutically acceptable salts thereof "promotes proliferation of pluripotent stem cells while maintaining an undifferentiated state under feeder-free conditions" means that the number of cells exceeding 100% can be obtained by adding at least one selected from the group consisting of ethanolamine and/or ethanolamine analogs and pharmaceutically acceptable salts thereof to the medium, wherein the number of pluripotent stem cells cultured under the same conditions except that ethanolamine and/or ethanolamine analogs and pharmaceutically acceptable salts thereof are not added and in the absence of a feeder cell is the standard (100%). Whether it promotes proliferation of pluripotent stem cells while maintaining an undifferentiated state under feeder-free conditions can be evaluated by a method using a known cell proliferation system, such as the method described in Examples and the like.

High concentration of β-mercaptoethanol is feared for its toxicity. Therefore, the concentration of β-mercaptoethanol used in the present invention is not more than 9 μM, more preferably not more than 7 μM, further preferably not more than 5 μM, as the final concentration when in use. Furthermore, substantial or complete absence of β-mercaptoethanol is preferable. In the present invention, pluripotent stem cell can be stably proliferated while maintaining an undifferentiated state even when β-mercaptoethanol is not contained substantially.

The definition of the "substantial absence of β-mercaptoethanol" is as mentioned above.

The medium used in the present invention may be further added with albumin. Addition of albumin affords a preservation stabilizing effect on the medium, as well as enhances the effect of ethanolamine to promote proliferation of pluripotent stem cells while maintaining an undifferentiated state.

The "preservation stabilization" of the medium means alleviation of the time-dependent deterioration of the medium during preservation of the medium (generally, about −80° C. to about 40° C.) and when in use. The "deterioration of the medium" in the present invention means deterioration of the function to proliferate pluripotent stem cells while maintaining an undifferentiated state, and the level thereof can be evaluated by culturing pluripotent stem cells in said medium for a given period, and counting the cell number, as described in the below-mentioned Examples. Use of a medium immediately after preparation being the standard, a smaller cell number after culture is evaluated as further deterioration of the medium.

The albumin to be used in the present invention is an animal-derived serum albumin. Examples of the animal include, but are not particularly limited to, rodents such as mouse, rat, hamster, guinea pig and the like, experiment animals such as rabbit and the like, pets such as dog, cat and the like, domestic animals such as bovine, swine, goat, horse, sheep and the like, primates such as human, monkey, orangutan, chimpanzee and the like, and the like. When cells to be used for regenerative medicine are cultured, the albumin to be used in the present invention is preferably human albumin. Being "animal-derived" means that the amino acid sequence of the albumin is that of an animal.

The albumin used in the present invention may be isolated and purified from a biological sample of an animal (e.g., blood, plasma, serum etc.), or isolated and purified after production by gene recombination technology. The preparation method of albumin is known. In addition, albumin may be a commercially available product and can be obtained from, for example, Sigma-Aldrich Co. LLC, and the like.

The albumin used in the present invention is preferably obtained from plasma of an animal (including human) or by gene recombination technology.

The albumin used in the present invention carries fatty acid in an amount of preferably not more than 9 mg/g, more preferably not more than 7 mg/g, further preferably not more than 2.2 mg/g.

When a medium added with albumin is used in the present invention, the final concentration (concentration when in use) of albumin in the medium is not particularly limited as long as it affords a medium-stabilizing effect, and enhances a promoting effect of at least one selected from the group consisting of ethanolamine, ethanolamine analogs and pharmaceutically acceptable salts thereof on the proliferation of pluripotent stem cells while maintaining an undifferentiated state. It is generally 0.1 g/l to 20 g/l, preferably 1 g/l to 8 g/l.

The medium to be used in the present invention may be further added with sulfated saccharides and/or a pharmaceutically acceptable salt thereof. Addition of sulfated saccharides in combination with ethanolamine to the medium affords a stabilizing effect on the medium, as well as enhances the effect of ethanolamine to promote proliferation of pluripotent stem cells while maintaining an undifferentiated state. When desired, plural kinds of sulfated saccharides and/or pharmaceutically acceptable salts thereof may be used.

In the present invention, the "sulfated saccharide" is sulfated substance of saccharides. The "saccharide" is not particularly limited as long as it is known in the technical field, or may be novel. The saccharide may be a natural product or synthesized product. The sulfated saccharides to be added to the medium of the present invention preferably include sulfated monosaccharide, sulfated disaccharide, sulfated polysaccharide, sulfated sugar alcohol and sulfated cyclitol.

The "monosaccharide" may be known in the technical field or novel. The number of carbons constituting carbohydrate is not limited and may be any of, for example, tetrose, pentose, hexose, heptose and the like. Specific examples of the monosaccharide include glucose, galactose, mannose, talose, idose, altrose, allose, gulose, xylose, arabinose, rhamnose, fucose, fructose, ribose, deoxyribose, glucosamine, galactosamine, glucuronic acid, galacturonic acid and the like. The sulfated monosaccharide is sulfated substance of these monosaccharides.

The "disaccharide" is a carbohydrate wherein two molecules of the aforementioned monosaccharide are bonded by a glycosidic bond to become one molecule, and may be known in the technical field or novel. The manner of glycosidic bond is not particularly limited, and may be any of α-1,2 bond, β-1,2 bond, α-1,3 bond, β-1,3 bond, α-1,4 bond, β-1,4 bond, α-1,5 bond, β-1,5 bond, α-1,6 bond, β-1,6 bond, α-1, α-1 bond, α-1, β-1 bond, α-1, β-2 bond and the like. Specific examples of the disaccharide include sucrose, lactose, maltose, trehalose, cellobiose, maltitol and the like. The sulfated disaccharide is sulfated substance of these disaccharides.

The polysaccharide is a carbohydrate wherein three or more molecules of the aforementioned monosaccharide are bonded by a glycosidic bond to become one molecule, and may be known in the technical field or novel. Polysaccharide may consist of only one kind of the aforementioned saccharides, or two or more kinds thereof may be combined.

Polysaccharide may be any of linear, branched and cyclic. Examples of the polysaccharide include amylose, amylopectin, glycogen, dextrin, α-cyclodextrin, β-cyclodextrin, γ-cyclodextrin, dextran, maltoheptaose, stachyose, maltotriose, pullulan, cellulose and a derivative thereof (e.g., hydroxyethylcellulose, hydroxypropylcellulose etc.), laminaran, curdlan, callose, mannan, glucomannan, galactomannan, xylan, glucuronoxylan, arabinoxylan, araban, galactan, galacturonan, chitin, chitosan, xyloglucan, pectic acid and pectin, alginic acid, arabinogalactan, glycosaminoglycan (e.g., dextran sulfate, heparan sulfate, heparin, hyaluronic acid, chondroitin 4-sulfate, chondroitin 6-sulfate, dermatan sulfate, ketaran sulfate etc.), guar gum, xanthan gum, fucoidan, inulin and the like. The sulfated polysaccharide is sulfated substance of these polysaccharides. Among the above-mentioned saccharides, those already sulfated (e.g., dextran sulfate, heparan sulfate, heparin, chondroitin 4-sulfate, chondroitin 6-sulfate, dermatan sulfate, ketaran sulfate, fucoidan etc.) include the saccharides themselves. As the sulfated polysaccharide, dextran sulfate, sulfated substance of cellulose (i.e., cellulose $SO_3H$), sulfated substance of xanthan gum (i.e., xanthan gum $SO_3H$), fucoidan, sulfated substance of alginic acid (i.e., alginate $SO_3H$), sulfated substance of inulin (i.e., inulin $SO_3H$), sulfated substance of α-cyclodextrin (i.e., α-cyclodextrin $SO_3H$), sulfated substance of maltoheptaose (i.e., maltoheptaose $SO_3H$), sulfated substance of stachyose (i.e., stachyose $SO_3H$) and sulfated substance of maltotriose (i.e., maltotriose $SO_3H$) are preferable, and dextran sulfate is particularly preferable.

The "sugar alcohol" is a compound produced by reducing the carbonyl group of the aforementioned monosaccharide, and may be known in the technical field or novel. Examples of the sugar alcohol include glycerol, erythritol, threitol, arabinitol, xylitol, sorbitol, mannitol, volemitol, perseitol and the like, and erythritol, xylitol and mannitol are preferable. The sulfated sugar alcohol is a sulfated substance of these sugar alcohols.

The "cyclitol" is polyhydroxycycloalkane, and also called cyclic sugar alcohol or cyclit. The cyclitol may be known in the technical field or novel. While cyclitol is known to include many isomers, any isomer may be used. While the number of carbons constituting the ring is not particularly limited, a 6-membered ring is preferable. Examples of the cyclitol include inositol (1,2,3,4,5,6-cyclohexanehexaol), a derivative of inositol (derivative wherein hydroxy group is substituted by amino group, ketone group, carboxyl group etc.) and the like. The sulfated cyclitol is a sulfated substance of these cyclitols.

The sulfated saccharides to be added to the medium in the present invention may be in the form of a pharmaceutically acceptable salt. Examples of such salt include salts of a sulfate group etc. present in the sulfated saccharides and a base. Specific examples thereof include alkali metal salts such as sodium salt, potassium salt and the like; alkaline earth metal salts such as calcium salt, magnesium salt and the like; salts with inorganic base such as aluminum salt, ammonium salt and the like; salts with organic base such as trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like, which can be prepared from a free form by a conventional method. As the pharmaceutically acceptable salt of the sulfated saccharides, a sodium salt or potassium salt of a sulfate group is preferable. Examples thereof include sucrose $8SO_3K$, dextran sulfate Na (molecular weight 5,000, 25,000, 500,000 etc.), cellulose $SO_3Na$, xanthan gum $SO_3Na$, alginic acid $SO_3Na$, inulin $SO_3Na$, α-cyclodextrin $SO_3Na$, erythritol $SO_3Na$, mannitol $SO_3Na$, myo-inositol $6SO_3K$ and the like, and dextran sulfate Na is particularly preferable.

When a medium added with sulfated saccharides and/or a pharmaceutically acceptable salt thereof is used in the present invention, the final concentration (concentration when in use) of sulfated saccharides and/or a pharmaceutically acceptable salt thereof in the medium is not particularly limited as long as the medium stabilizing effect is afforded and a promoting effect of at least one selected from the group consisting of ethanolamine, ethanolamine analogs and pharmaceutically acceptable salts thereof on the proliferation of pluripotent stem cells while maintaining an undifferentiated state is enhanced. It is generally 1 to 1000 ng/ml, preferably 10 to 250 ng/ml. When plural kinds are used, the total amount thereof is set to fall within the above-mentioned range. However, it can be increased or decreased as appropriate depending on the kind.

The average molecular weight of sulfated saccharides or a pharmaceutically acceptable salt thereof is not particularly limited, and varies depending on the kind of the sulfated saccharides to be employed and the kind of the salt. It is generally 50 to 1,000,000, preferably 100 to 700,000, more preferably 300 to 500,000, most preferably 500 to 100,000. When the average molecular weight exceeds 1,000,000, addition thereof at a concentration not less than a given level tends to cause toxicity or suppression of cell proliferation seemingly due to the inhibition of cell adhesion and the like. The average molecular weight can be measured by gel permeation chromatography and the like.

For example, the average molecular weight of the dextran sulfate Na is generally 1000 to 700,000, preferably 1000 to 300,000, more preferably 1000 to 100,000, most preferably 2,500 to 7,500.

The medium to be used in the present invention may or may not contain serum. When cells to be used for regenerative medicine are cultivated, in view of the possibility of serum being a virus infection source, and concern about property difference between lots which causes inconsistent culture results and the like, culture is preferably performed under serum-free conditions.

The medium to be used in the present invention may or may not contain a component derived from a species different from the cell to be cultured. When human cells to be used for regenerative medicine are cultivated, a component derived from an animal other than human is preferably absent from the aspects of safety after transplantation.

As the basal medium to be used in the present invention, one known per se can be used depending on the kind of the pluripotent stem cells, and is not particularly limited as long as it does not inhibit proliferation of the pluripotent stem cells while maintaining an undifferentiated state. Examples thereof include DMEM, EMEM, IMDM (Iscove's Modified Dulbecco's Medium), GMEM (Glasgow's MEM), RPMI-1640, α-MEM, Ham's Medium F-12, Ham's Medium F-10, Ham's Medium F12K, Medium 199, ATCC-CRCM30, DM-160, DM-201, BME, Fischer, McCoy's 5A, Leibovitz's L-15, RITC80-7, MCDB105, MCDB107, MCDB131, MCDB153, MCDB201, NCTC109, NCTC135, Waymouth's MB752/1, CMRL-1066, Williams' medium E, Brinster's BMOC-3 Medium, E8 medium (Nature Methods, 2011, 8, 424-429), a mixed medium thereof and the like. In addition, a medium altered for culture of pluripotent stem cells, a mixture of the above-mentioned basal medium and other medium, and the like may also be used.

The medium to be used in the present invention can further contain an additive known per se. The additive is not particularly limited as long as it does not inhibit proliferation of pluripotent stem cells while maintaining an undifferentiated state. Examples thereof include growth factor (e.g., insulin etc.), iron source (e.g., transferrin etc.), polyamines (e.g., putrescine etc.), mineral (e.g., sodium selenate etc.), saccharides (e.g., glucose etc.), organic acid (e.g., pyruvic acid, lactic acid etc.), amino acid (e.g., L-glutamine etc.), reducing agent (e.g., sodium thioglycolate), vitamins (e.g., ascorbic acid, d-biotin etc.), steroid (e.g., β-estradiol, progesterone etc.), antibiotic (e.g., streptomycin, penicillin, gentamicin etc.), buffering agent (e.g., HEPES etc.) and the like. In addition, additives that have been conventionally used for culturing pluripotent stem cells can be contained as appropriate. The additive is preferably contained within a concentration range known per se.

In the culture method of the present invention, a feeder cell may or may not be used. When cells to be used for regenerative medicine are cultivated, from the aspect of safety after transplantation, a feeder cell is preferably absent (feeder-free). Although not bound by any theory, in the culture method of the present invention, proliferation of pluripotent stem cells while maintaining an undifferentiated state can be promoted even in the absence of a feeder cell, since ethanolamine generally secreted from a feeder cell is added to the medium.

When a feeder cell is not used, culture is preferably performed by using an extracellular matrix or an active fragment thereof or an artificial product mimicking the functions thereof.

The extracellular matrix is not particularly limited as long as it is generally used for cell culture with the aim to improve adhesion between the surface of a culture vessel and the cell. For example, known ones such as laminin (laminin 511, laminin 332 etc.), fibronectin, vitronectin, collagen, elastin, adhesamine and the like can be used. The active fragment of an extracellular matrix only needs to be a fragment thereof having a cell adhesion activity equivalent to that of the extracellular matrix, and known ones can be used. For example, E8 fragment of laminin 511, E8 fragment of laminin 332 and the like disclosed in JP-A-2011-78370 can be mentioned. The extracellular matrix and an active fragment thereof may be commercially available products and available from, for example, (Life Technologies, BD Falcon, BioLamina) and the like. Two or more kinds of these extracellular matrices and active fragments thereof may be used in combination. Also, a matrigel (trade name) which is a mixture of complicated basal lamina components containing protein and polysaccharides, that are extracted and purified from EHS sarcoma of mouse overproducing the basal lamina, may also be used. The extracellular matrix and an active fragment thereof may be suspended in a suitable solution, and applied to a container suitable for cultivating cells.

An artificial product mimicking the function of extracellular matrix is not particularly limited as long as it is generally used for culturing cells and, for example, known ones such as Synthemax (registered trade mark) and Ultra-Web (registered trade mark) of Corning Incorporated, Hy-STEM series, polylysine and polyornithine of Sigma Aldrich Co., Ltd. and the like can be used.

The extracellular matrix or an active fragment thereof or an artificial product mimicking the functions thereof to be used in the present invention are preferably matrigel or laminin 511 or an active fragment of laminin 511, more preferably an active fragment of laminin 511 (i.e., E8 fragment of laminin 511).

In the culture method of the present invention, the cell seeding method is not particularly limited, and may be colony seeding or single cell-seeding. To produce pluripotent stem cells for regenerative medicine at an industrial level, the work needs to be performed by plural workers under the conditions where procedures and schedule are rigorously managed. Therefore, single cell-seeding permitting rigorous adjustment of the seeding cell number is preferable.

For single cell-seeding, colonies of pluripotent stem cells are dissociated to single cells, and seeded in the medium. Single cell seeding can be performed by a method known per se. For example, cell-cell adhesion and cell-matrix adhesion are weakened with a cell detaching solution (trypsin solution etc.), and the cells are detached from the matrix with a scraper (IWAKI, 9000-220 etc.) and the like (in this state, the cells forming cell clusters are suspended in a solution, not complete single cells). The cells are thereafter dissociated by pipetting into single cells, and seeded in the medium. When seeding, ROCK inhibitor such as Y-27632 (Nacalai Tesque: 08945-84) and the like is preferably added to the medium to ensure survival of the pluripotent stem cells. Since ROCK inhibitor is not necessary for the proliferation of pluripotent stem cells from the following day of the seeding, it is preferably excluded from the medium.

Other culture conditions can be appropriately determined. For example, while the culture temperature is not particularly limited, it can be about 30 to 40° C., preferably about 37° C. The $CO_2$ concentration can be about 1 to 10%, preferably about 2 to 5%. The oxygen partial pressure can be 1 to 10%.

In cell culture, medium change is sometimes necessary during the culture due to the deterioration of medium components, accumulation of waste products discharged from the cell and the like. In the culture method of the present invention, it is also possible to omit the medium change as shown in the Examples. For example, pluripotent stem cells can be cultivated for 4 or more consecutive days (4 days, 5 days, 6 days etc.) without medium change.

In one embodiment, the present invention provides a culture method for the proliferation of a pluripotent stem cell while maintaining an undifferentiated state, comprising a step of cultivating a pluripotent stem cell in a medium added with at least one selected from the group consisting of ethanolamine, ethanolamine analogs and pharmaceutically acceptable salts thereof, and added with sulfated saccharides and/or a pharmaceutically acceptable salt thereof. The definitions of ethanolamine, ethanolamine analogs and pharmaceutically acceptable salts thereof, and sulfated saccharides and a pharmaceutically acceptable salt thereof in the culture method are the same as those mentioned above, and use concentrations thereof are also as mentioned above. In addition, other conditions relating to the culture method are also as mentioned above.

Preservation stabilizing method for medium for proliferation of pluripotent stem cells.

The present invention provides a preservation stabilizing method for a medium for the proliferation of a pluripotent stem cell, comprising adding at least one selected from the group consisting of ethanolamine, ethanolamine analogs and pharmaceutically acceptable salts thereof, and adding sulfated saccharides and/or a pharmaceutically acceptable salt thereof (hereinafter to be also referred to as the stabilizing method of the present invention).

The "preservation stabilization" of the medium in the present invention means alleviation of the time-dependent deterioration of the medium during preservation of the medium (generally, about −80° C. to 40° C.). The "deterioration of the medium" here means deterioration of the function to proliferate pluripotent stem cells while maintaining an undifferentiated state, and the level thereof can be evaluated by culturing pluripotent stem cells in said medium for a given period, and counting the cell number, as described in the below-mentioned Examples. Use of a medium immediately after preparation being the standard, a smaller cell number after culture is evaluated as further deterioration of the medium.

The medium for the proliferation of pluripotent stem cells in the present invention is the same as the medium used in the above-mentioned culture method of the present invention, and preferably a medium for the proliferation of pluripotent stem cells while maintaining an undifferentiated state.

Ethanolamine and ethanolamine analogs and pharmaceutically acceptable salts thereof to be added to the medium for preservation stability of the medium are the same as those used for the above-mentioned culture method of the present invention. The concentration of addition to the medium is the same as those in the above-mentioned culture method of the present invention. By adding ethanolamine and ethanolamine analogs and pharmaceutically acceptable salts thereof to the medium, the medium after addition can be stabilized.

The stabilizing method of the present invention further comprises a step of adding sulfated saccharides and/or a pharmaceutically acceptable salt thereof. The sulfated saccharides and/or a pharmaceutically acceptable salt thereof are the same as those used for the above-mentioned culture method of the present invention. The concentration of addition to the medium is the same as that in the above-mentioned culture method of the present invention. By adding at least one selected from the group consisting of ethanolamine, ethanolamine analogs and pharmaceutically acceptable salts thereof, and sulfated saccharides and/or a pharmaceutically acceptable salt thereof in combination to the medium, the stability of the medium can be further enhanced.

According to the present invention, for example, when the medium is preserved at room temperature (generally about 15 to 25° C.) for up to about 8 days, after preparation of the medium, deterioration of the medium can be alleviated. Hence, the medium can be preserved for a longer term than before, and the present invention is useful for the production of pluripotent stem cells and the like.

Medium additive for proliferation of pluripotent stem cells while maintaining an undifferentiated state.

The component to be added to the basal medium in the above-mentioned culture method of the present invention can be a medium additive. That is, the present invention provides a medium additive for the proliferation of a pluripotent stem cell while maintaining an undifferentiated state, comprising at least one selected from the group consisting of ethanolamine, ethanolamine analogs and pharmaceutically acceptable salts thereof, and substantially free of β-mercaptoethanol or containing β-mercaptoethanol at a concentration of not more than 9 µM when in use (hereinafter to be also referred to as the medium additive of the present invention).

Ethanolamine and ethanolamine analogs and pharmaceutically acceptable salts thereof are the same as those used for the above-mentioned culture method of the present invention.

The amount of the medium additive of the present invention to be added to a medium can be determined to fall within any range as long as it can promote proliferation of pluripotent stem cells while maintaining an undifferentiated state when cultured under feeder-free conditions using the medium after preparation. It can be added such that the final concentration of ethanolamine and ethanolamine analogs and pharmaceutically acceptable salts thereof in the medium is generally 1 µM to 1000 µM, preferably 5 µM to 200 µM, or 11 µM to 200 µM.

High concentration ercaptoethanol is feared for its toxicity. Therefore, the concentration of β-mercaptoethanol used in the present invention is not more than 9 µM, more preferably not more than 7 µM, further preferably not more than 5 µM, as the final concentration when in use. Furthermore, substantial or complete absence of β-mercaptoethanol is preferable. In the present invention, pluripotent stem cell can be stably proliferated while maintaining an undifferentiated state even when β-mercaptoethanol is not contained substantially.

The definition of the "substantially free of β-mercaptoethanol" is as mentioned above.

The medium additive of the present invention may further contain albumin, sulfated saccharides and/or a pharmaceutically acceptable salt thereof. These are the same as those used for the above-mentioned culture method of the present invention.

Where necessary, the medium additive of the present invention may contain other components other than the above-mentioned components. Examples of other components include, but are not particularly limited to, additives generally used for the preparation of a medium, for example, additives contained in the medium used in the above-mentioned production method of the present invention.

While the medium additive of the present invention may or may not contain a component derived from a species different from the cell to be cultured. When human cells to be used for regenerative medicine are cultivated, it is preferable that a component derived from an animal other than human not be contained.

Using the medium additive of the present invention, a medium capable of stable proliferation for a long term while maintaining an undifferentiated state even in serum-free, feeder-free and single cell-seeding culture can be prepared.

Other features of the invention will become apparent in the course of the following descriptions of exemplary embodiments which are given for illustration of the invention and are not intended to be limiting thereof.

EXAMPLES

In the following Examples, proliferation effects of various test compounds on human pluripotent stem cells were evaluated. As human pluripotent stem cells, induced pluripotent stem cells (iPS cells, 201B7 strain) purchased from iPS Academia Japan, Inc. were used, unless particularly specified. Cell culture was performed using a culture vessel (Becton, Dickinson and Company, Falcon culture petri dish or Falcon culture plate) coated with a basal lamina matrix under the conditions of 5% $CO_2$/37° C.

Various test compounds were added to a medium having the "E8" composition (disclosed in Nature Methods, 2011, 8, 424-429, which is incorporated herein by reference in its entirety) considered at present to be the minimum composition for cultivating human pluripotent stem cells at given concentrations and used for culture, and the effects thereof were studied. The medium was prepared by using Essential 8 (Life Technologies: A14666SA) considered to have the "E8" composition or a medium formulated to have an equivalent composition.

Reference Example 1

Medium Stabilizing Effect of Albumin

Human serum-derived albumin (Sigma-Aldrich Co. LLC: A1887) was added at a final concentration of 2.6 g/l, and the effect of albumin was examined by studying the cell numbers after culture when used immediately after preparation for culture or when used after preservation at 4° C. for 3 weeks after the preparation. The culture period was 1 week. 13,000 viable cells per well were used for single cell seeding. As a basal lamina matrix, a fragment containing an active domain of laminin 511, which was purchased from Osaka University, was applied at 5 µg/well. Y-27632 (final concentration 10 µM, Nacalai Tesque: 08945-84) was added to the medium used for seeding. The cells were cultured in a medium free of Y-27632 from the following day. Viable cell number was measured by Trypan Blue (Life Technologies: 15250-061) staining using a hemocytometer.

The average results of 3 series of experiments for each medium are shown in FIG. 1. When used immediately after preparation, equivalent cell proliferation was observed with or without albumin addition. When a medium after 3 weeks from preparation was used, cell proliferation was scarcely found in an albumin-free medium, whereas obvious cell proliferation was observed in an albumin addition medium. The above results reveal that E8 minuimun composition medium shows remarkable degradation of the property when kept under general use (preservation) conditions for 3 weeks, but addition of albumin can improve such deteriorative phenomenon. To conclude, albumin was found to contribute to the stabilization of a medium stored at 4° C.

Example 1. Proliferation Promoting Effect of Ethanolamine and Combination Effect with Albumin Ethanolamine (Sigma-Aldrich Co. LLC: E0135) was added at a final concentration of 6, 30, 150, 750 or 3,750 µM, and the medium was used for culture immediately after preparation, and the effect of ethanolamine was examined by studying the cell numbers after culture. The culture period was 1 week. To study the effect of combination with albumin, human serum-derived albumin (Sigma-Aldrich Co. LLC: A1887) was further added at a final concentration of 2.6 g/l to the above-mentioned ethanolamine addition medium, and a similar examination was performed. 13,000 viable cells per 1 well were used for single cell-seeding. As a basal lamina matrix, a fragment containing the active domain of laminin 511, which was purchased from Osaka University, was applied at 5 µg/well. Y-27632 was added (final concentration 10 µM, Nacalai Tesque: 08945-84) to the medium used for seeding. The cells were cultured in a medium free of Y-27632 from the following day. The number of viable cells was measured by Trypan Blue (Life Technologies: 15250-061) staining using a hemocytometer.

Figure 2:
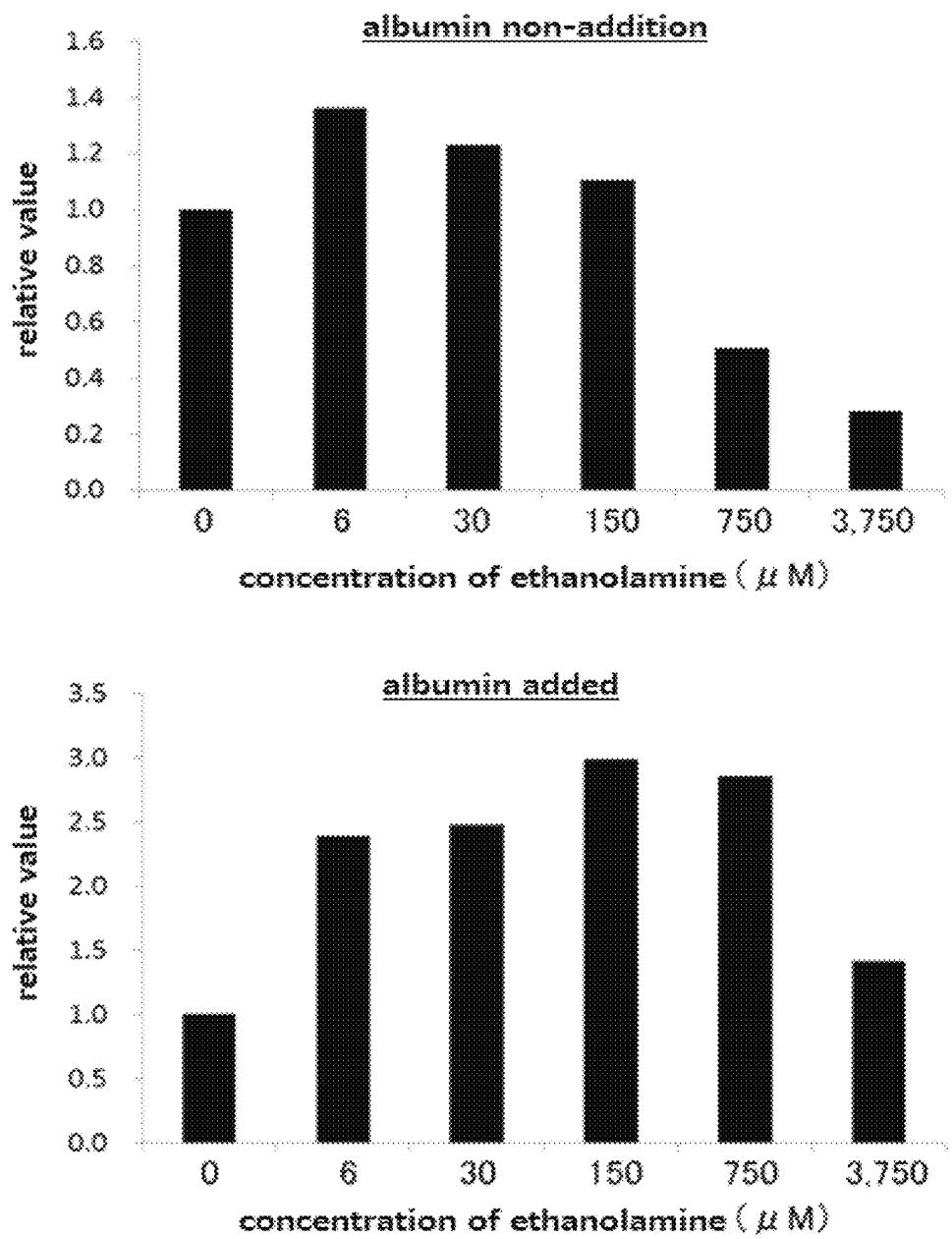
FIG. 2 shows a cell proliferation promoting effect of ethanolamine and an effect of combination with albumin.

The experiment was performed in 3 series for each medium, and the average results are shown in FIG. 2. The values are shown as relative values to the ethanolamine non-addition group (0 µM). Ethanolamine was found to show a proliferation-promoting effect in a relatively wide concentration range. It was found that a proliferation suppressive effect conversely appears in a high concentration range. It was found that combination with albumin further enhances the proliferation promoting effect of ethanolamine, resists a proliferation suppressive effect in a high concentration range, and shows a proliferation promoting effect.

Example 2. Effect of Dextran Sulfate

Human serum derived albumin (Sigma-Aldrich Co. LLC: A1887) was added to a medium (final concentration 2.6 g/l), ethanolamine (final concentration 30 µM) was added singly thereto, dextran sulfate sodium (Wako Pure Chemical Industries, Ltd., final concentration 50 ng/ml) was further added to the medium, and a further proliferation promoting effect of a combination of ethanolamine and dextran sulfate sodium was verified. Culture was performed for about 3 weeks, which included two passages, and the cumulative viable cell increase rate for the total culture period was calculated. 13,000 viable cells per 1 well were used for single cell-seeding. As a basal lamina matrix, a fragment containing the active domain of laminin 511, which was purchased from Osaka University, was applied at 5 µg/well. Y-27632 was added (final concentration 10 µM, Nacalai Tesque: 08945-84) to the medium used for seeding. The cells were cultured in a medium free of Y-27632 from the following day. When passaged, cells were detached by TrypLE™ Select (Life Technologies: 12563-011), 13,000 viable cells were seeded again in Y-27632 added medium, and cultured in a medium free of Y-27632 from the following day. The number of viable cells was measured by Trypan Blue (Life Technologies: 15250-061) staining using a hemocytometer.

Figure 3:
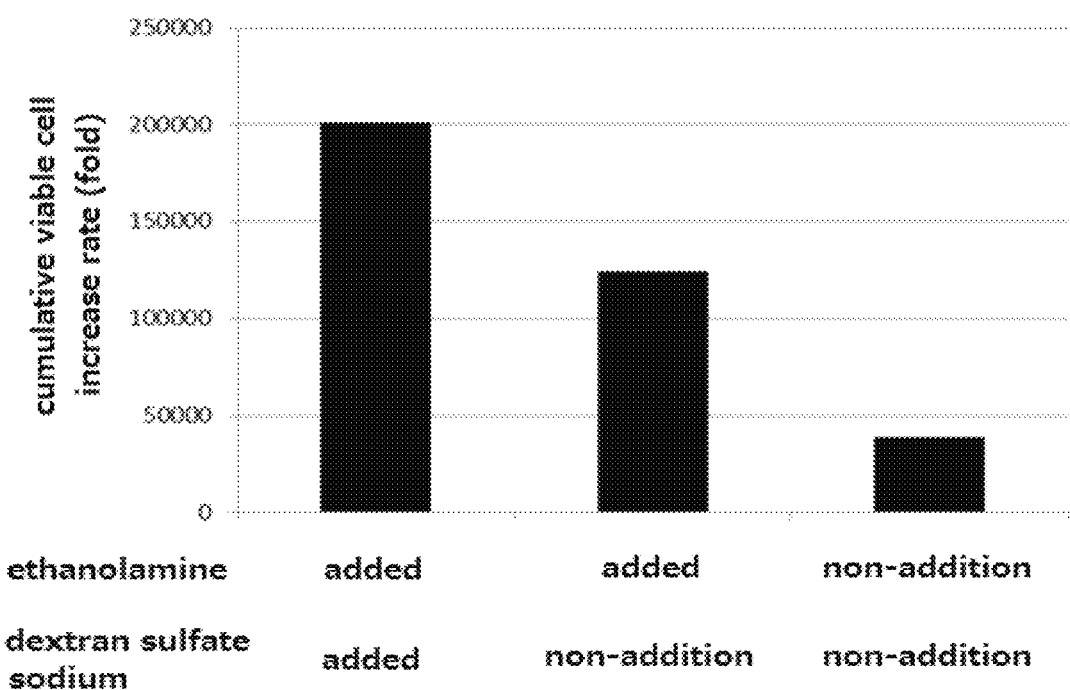
FIG. 3 shows a cell proliferation promoting effect by a combination of ethanolamine and dextran sulfate sodium, which is expressed by a cumulative viable cell increase rate (fold).

The experiment was performed in 3 series for each medium, and the average results are shown in FIG. 3. It was found that the cell increase rate was higher when dextran sulfate sodium was combined than the single addition of ethanolamine.

Figure 4:
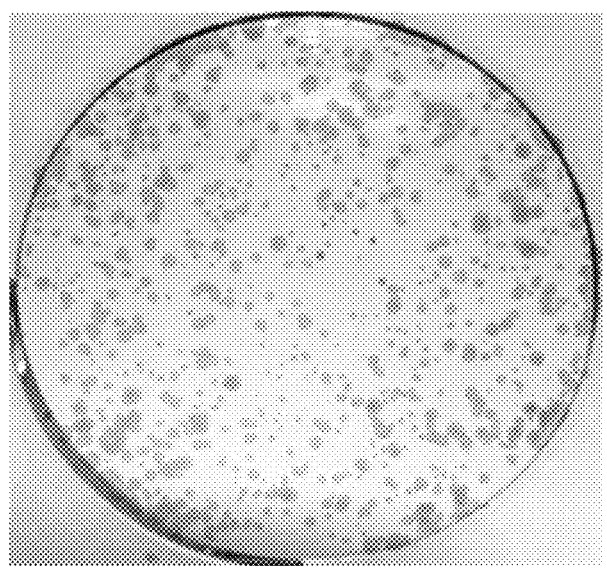
FIG. 4 shows the results of alkaline phosphatase staining of iPS cell colonies after long-term culture in an E8 minimum composition medium added with albumin, ethanolamine and dextran sulfate sodium.

Both ethanolamine and dextran sulfate sodium, which showed the highest increase rate, were added to a medium, and culture was performed for about one month. Alkaline phosphatase staining was performed to confirm maintenance of undifferentiated state. The results of staining with an alkaline phosphatase staining kit (Sigma-Aldrich Co. LLC: 86-R) are shown in FIG. 4. iPS cell colonies in the whole well were stained, which confirmed that long-term culture in an E8 minimum composition medium added with albumin, ethanolamine, dextran sulfate sodium resulted in the proliferation of iPS cells while maintaining an undifferentiated state.

Example 3. Proliferation Promoting Effect of Ethanolamine—Results of Culture Using Matrigel Ethanolamine (Sigma-Aldrich Co. LLC: E0135) was added at a final concentration of 6, 30, 150, 750 or 3,750 µM, and the medium was used for culture immediately after preparation, and the effect of ethanolamine was examined by studying the cell numbers after culture. The culture period was 8 days. 100,000 cells per 1 well were used for single cell-seeding. As a basal lamina matrix, matrigel (Japan Becton Dickinson) was applied. Y-27632 was added (final concentration 10 µM, Nacalai Tesque: 08945-84) to the medium used for seeding. The cells were cultured in a medium free of Y-27632 from the following day.

Figure 5:
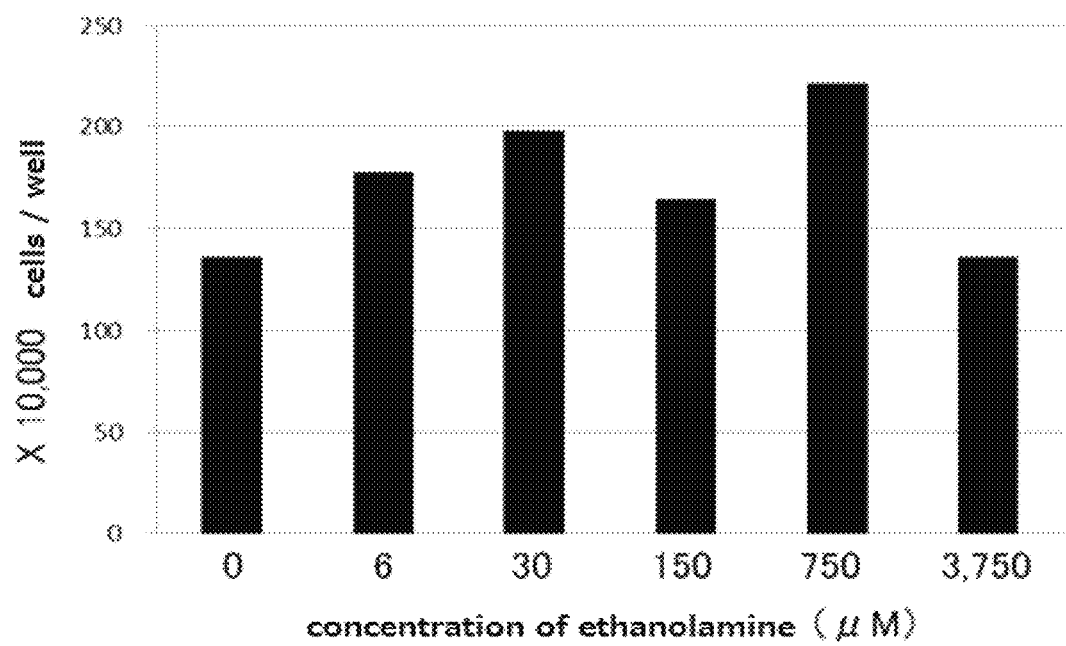
FIG. 5 shows a cell proliferation promoting effect of ethanolamine in culture using matrigel as a basal lamina matrix.

The experiment was performed in 3 series for each medium, and the average results are shown in FIG. 5. In the same manner as in Example 1, the results showing that ethanolamine affords a proliferation promoting effect in a wide concentration range were obtained. Therefore, it was found that the proliferation promoting effect of ethanolamine is not limited to culture using laminin 511.

Example 4. Effect of Combination of Ethanolamine and Dextran Sulfate Sodium-Results of Culture Using Matrigel (1) Effect in Medium Containing Albumin.

Essential 8 medium added with human serum derived albumin (final concentration 2.6 g/l) and ethanolamine (final concentration 30 μM) (control), and the medium added with dextran sulfate sodium at a given concentration were prepared, and the effect of combination of ethanolamine and dextran sulfate sodium was verified. The culture period was 6 to 12 days. For single cell-seeding, 40,000 cells per 1 well were seeded on a 12-well culture plate coated with matrigel. Y-27632 was added (final concentration 10 μM, Nacalai Tesque: 08945-84) to the medium used for seeding. The cells were cultured in a medium free of Y-27632 from the following day. For seeding as colony, the cells diluted 2.5- to 3.5-fold of the original culture per well were plated on a 6 well culture plate coated with matrigel. In this case, Y-27632 was not added to the medium to be used for seeding. The medium change was performed every 2 to 3 days.

The evaluation criteria of cell proliferation were as follows.
⊙: cell number is not less than 120% of that of control
○: cell number is not less than 100% and less than 120% of that of control
–: cell number is not less than 50% and less than 100% of that of control
x: cell number is not more than 50% of that of control The experiment was performed in 3 series for each medium, and the results are shown in Table 1. Higher cell proliferation was observed when dextran sulfate sodium was added. Therefore, it was found that the cell proliferation promoting effect afforded by a combination of ethanolamine and dextran sulfate sodium is not limited to culture using laminin 511. It was also found that the effect was exhibited even when seeded as colony, and the effect is not limited to single cell-seeding.

TABLE 1

| | final concentration (ng/ml) of dextran sulfate sodium | | | |
| --- | --- | --- | --- | --- |
| | 1 | 10 | 50 | 100 |
| single cell-seeding | ○ | ○ | ⊙ | not evaluated |
| colony seeding | not evaluated | ⊙ | not evaluated | ⊙ |

(2) Effect of Omission of Medium Change.

In the evaluation of the above-mentioned (1), culture was performed in a medium added with dextran sulfate sodium (final concentration 10 ng/ml) without medium change, and whether medium change can be omitted by adding ethanolamine and dextran sulfate sodium in combination to the medium was verified. The culture period was 6 days.

Figure 6:
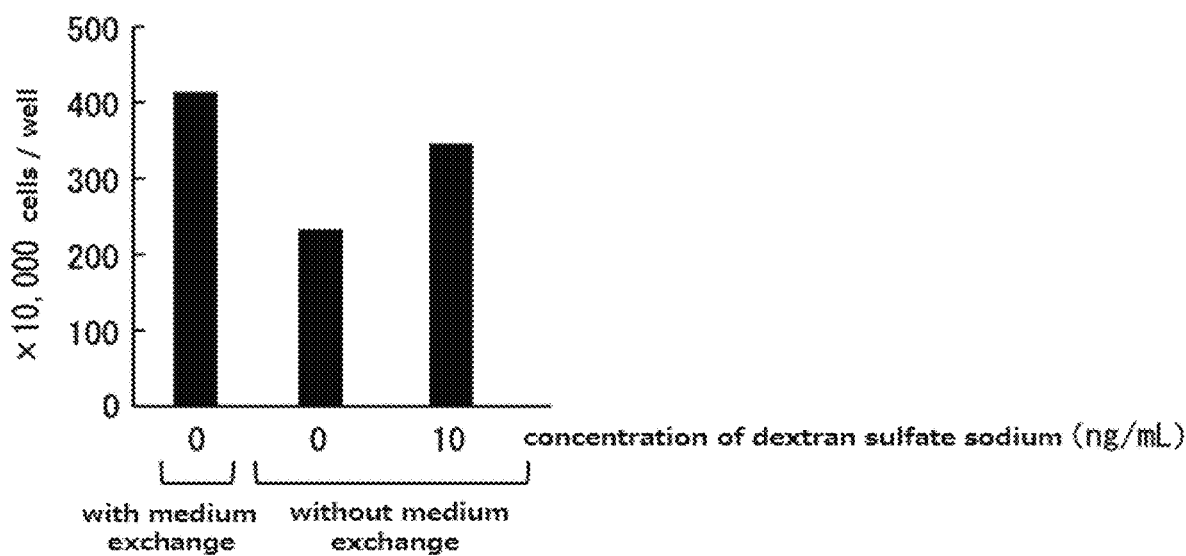
FIG. 6 shows that medium change can be omitted in culture of iPS cells, by adding dextran sulfate sodium to a medium containing albumin and ethanolamine.

The experiment was performed in 3 series for each medium, and the results are shown in FIG. 6. When medium change was not performed, high cell proliferation was found by the addition of dextran sulfate sodium. The effect thereof was close to that afforded by medium change with a medium free of dextran sulfate sodium. Therefore, it was found that a combination of ethanolamine and dextran sulfate sodium provides an effect of omitting medium change.

(3) Stabilizing Effect in Medium without Albumin.

Essential 8 medium added with ethanolamine (final concentration 30 μM) alone, the medium added with ethanolamine (final concentration 30 μM) and dextran sulfate sodium (Wako Pure Chemical Industries, Ltd., final concentration 50 ng/ml), and the medium added with human serum derived albumin (final concentration 2.6 g/l) alone were prepared, and a medium stabilizing effect of a combination of ethanolamine and dextran sulfate sodium was verified. Each medium was left standing at room temperature for 8 days after preparation and used for culture. The culture period was 8 days. 100,000 cells per 1 well were used for single cell-seeding on a 6-well culture plate coated with matrigel. Y-27632 was added (final concentration 10 μM, Nacalai Tesque: 08945-84) to the medium used for seeding. The cells were cultured in a medium free of Y-27632 from the following day.

Figure 7:
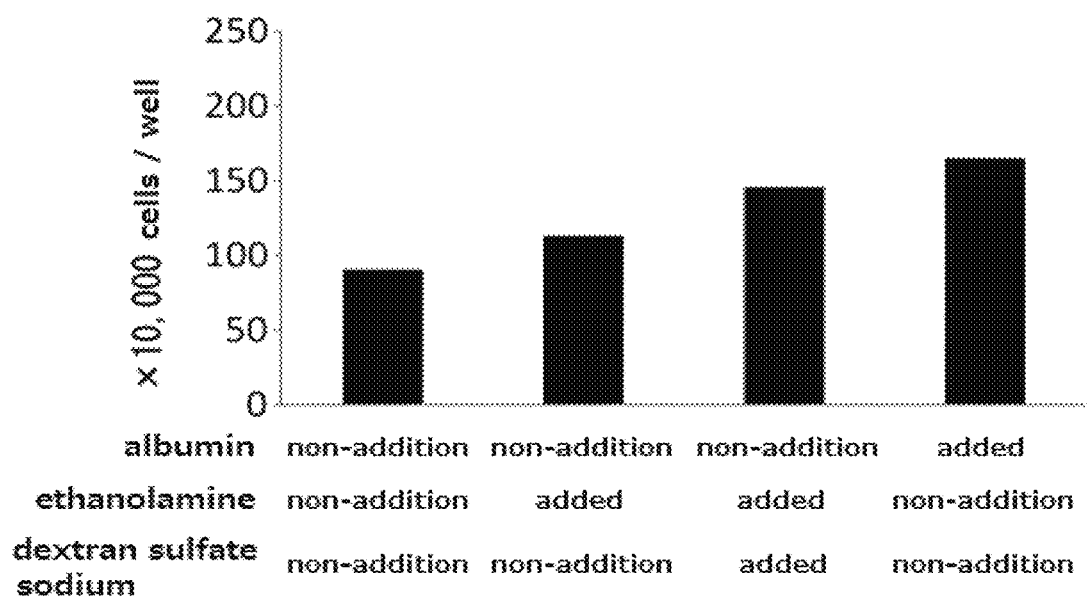
FIG. 7 shows a medium stabilizing effect of a combination of ethanolamine and dextran sulfate sodium under room temperature preservation conditions.

The experiment was performed in 3 series for each medium, and the average results are shown in FIG. 7. The effect afforded by adding both ethanolamine and dextran sulfate sodium was equal to that afforded by adding albumin. Therefore, it was found that a combination of ethanolamine and dextran sulfate sodium provides a medium stabilizing effect at room temperature, and has a possibility of replacing or reducing albumin widely used for medium.

Example 5. Effect of Ethanolamine Analogs (1) Effect of O-phosphoryl ethanolamine (aka phosphoethanolamine).

To a medium added with human serum-derived albumin (Sigma-Aldrich Co. LLC.: A1887) at a final concentration of 2.6 g/l was added O-phosphoryl ethanolamine (Sigma-Aldrich Co. LLC.: P0503-25G) at a final concentration of 6, 30, 150 or 750 μM, and used for the culture from the next day of preparation. After the culture, the cell number was counted to examine the effect of O-phosphoryl ethanolamine. The culture period was set to 1 week. 13,000 viable cells per well were used for single cell-seeding. As a basal lamina matrix, a fragment containing the active domain of laminin 511, which was purchased from Osaka University, was applied at 4.8 μg/well. Y-27632 was added (final concentration 10 μM, Nacalai Tesque: 08945-84) to the medium used for seeding. The cells were cultured in a medium free of Y-27632 from the following day. The number of viable cells was measured by Cell Viability autoanalyzer ViCELL™ XR (BECKMAN COULTER).

Figure 8:
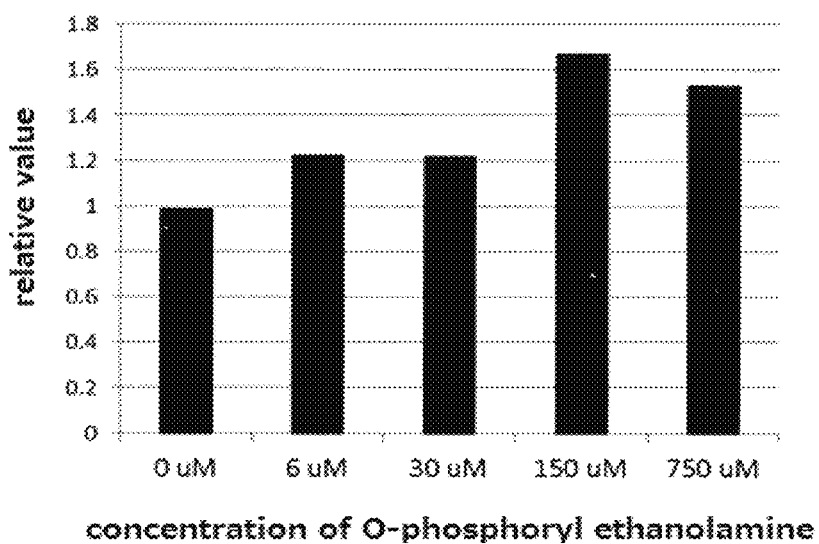
FIG. 8 shows a cell proliferation promoting effect of O-phosphoryl ethanolamine.

The experiment was performed in 3 series for each medium, and the average results are shown in FIG. 8. The values are shown as relative values to the O-phosphoryl ethanolamine non-addition group (0 μM). O-phosphoryl ethanolamine was found to show a proliferation-promoting effect in a relatively wide concentration range.

(2) Effect of 2-(methylamino)ethanol.

To a medium added with human serum-derived albumin (Sigma-Aldrich Co. LLC.: A1887) at a final concentration of 2.6 g/l was added 2-(methylamino)ethanol (Sigma-Aldrich Co. LLC.: 471445-25ML) at a final concentration of 6, 30, 150 or 750 μM, and used for the culture from the next day of preparation. After the culture, the cell number was counted to examine the effect of 2-(methylamino)ethanol. The culture period was set to 1 week. 13,000 viable cells per well were used for single cell-seeding. As a basal lamina matrix, a fragment containing the active domain of laminin 511, which was purchased from Osaka University, was applied at 4.8 μg/well. Y-27632 was added (final concentration 10 μM, Nacalai Tesque: 08945-84) to the medium used for seeding. The cells were cultured in a medium free of Y-27632 from the following day. The number of viable cells was measured by Cell Viability autoanalyzer ViCELL™ XR (BECKMAN COULTER).

Figure 9:
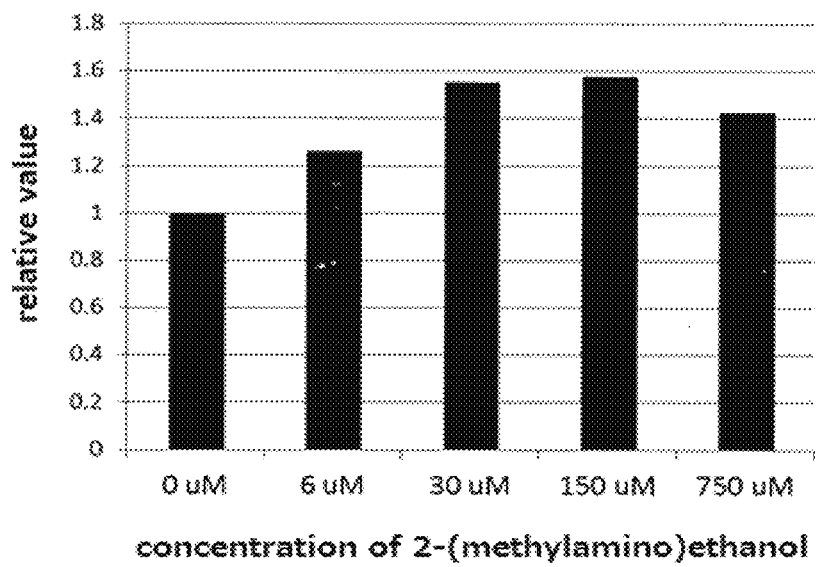
FIG. 9 shows a cell proliferation promoting effect of 2-(methylamino)ethanol.

The experiment was performed in 3 series for each medium, and the average results are shown in FIG. 9. The values are shown as relative values to the 2-(methylamino) ethanol non-addition group (0 μM). 2-(Methylamino)ethanol was found to show a proliferation-promoting effect in a relatively wide concentration range.

(3) Effect of 2-dimethylaminoethanol.

To a medium added with human serum-derived albumin (Sigma-Aldrich Co. LLC.: A1887) at a final concentration of 2.6 g/l was added 2-dimethylaminoethanol (Sigma-Aldrich Co. LLC.: 471453-100 ml) at a final concentration of 6, 30, 150 or 750 μM, and used for the culture from the next day of preparation. After the culture, the cell number was counted to examine the effect of 2-dimethylaminoethanol. The culture period was set to 1 week. 13,000 viable cells per well were used for single cell-seeding. As a basal lamina matrix, a fragment containing the active domain of laminin 511, which was purchased from Osaka University, was applied at 4.8 μg/well. Y-27632 was added (final concentration 10 μM, Nacalai Tesque: 08945-84) to the medium used for seeding. The cells were cultured in a medium free of Y-27632 from the following day. The number of viable cells was measured by Cell Viability autoanalyzer ViCELL™ XR (BECKMAN COULTER).

Figure 10:
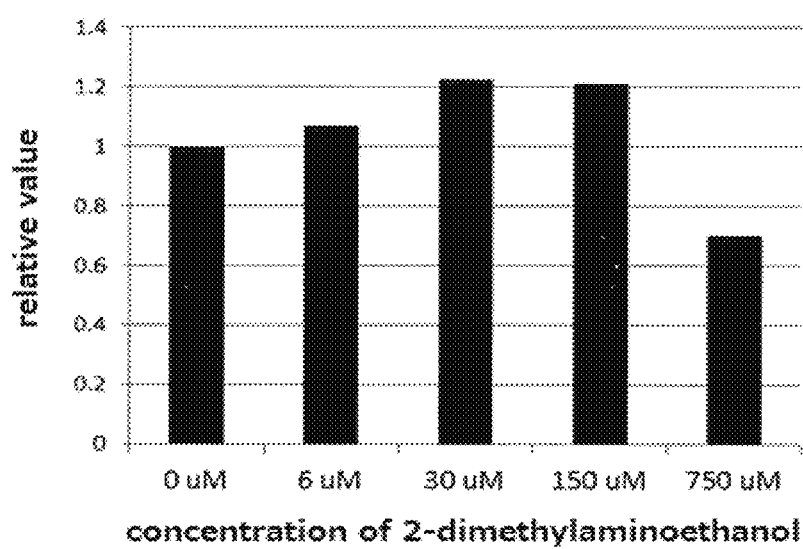
FIG. 10 shows a cell proliferation promoting effect of 2-dimethylaminoethanol.

The experiment was performed in 3 series for each medium, and the average results are shown in FIG. 10. The values are shown as relative values to the 2-dimethylaminoethanol non-addition group (0 μM). It was found that 2-dimethylaminoethanol shows a proliferation promoting effect in a relatively wide concentration range, but a proliferation suppressive effect appears in a high concentration range.

(4) Effect of Ethanolamine Hydrochloride.

To a medium added with human serum-derived albumin (Sigma-Aldrich Co. LLC.: A1887) at a final concentration of 2.6 g/l was added ethanolamine hydrochloride (Tokyo Chemical Industry Co., Ltd.: A0298) at a final concentration of 6, 30, 150 or 750 μM, and used for the culture from the next day of preparation. After the culture, the cell number was counted to examine the effect of ethanolamine hydrochloride. The culture period was set to 1 week. 13,000 viable cells per well were used for single cell-seeding. As a basal lamina matrix, a fragment containing the active domain of laminin 511, which was purchased from Osaka University, was applied at 4.8 μg/well. Y-27632 was added (final concentration 10 μM, Nacalai Tesque: 08945-84) to the medium used for seeding. The cells were cultured in a medium free of Y-27632 from the following day. The number of viable cells was measured by Cell Viability autoanalyzer ViCELL™ XR (BECKMAN COULTER).

Figure 11:
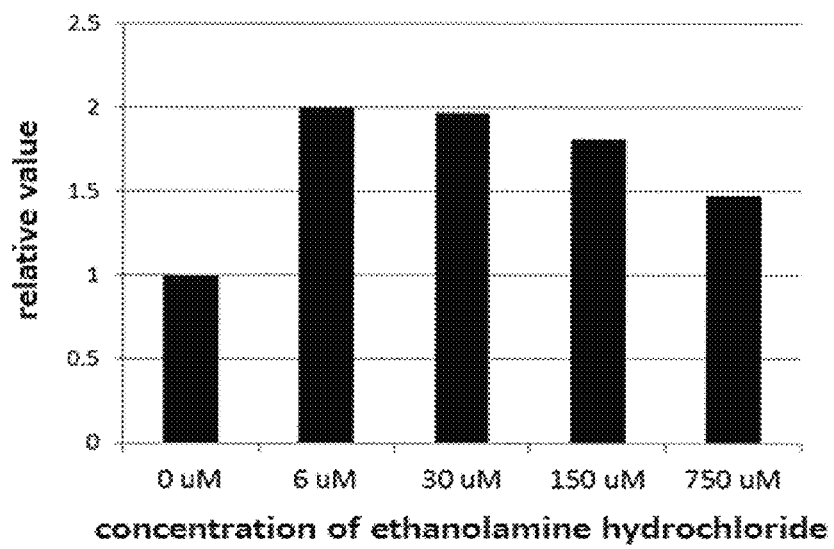
FIG. 11 shows a cell proliferation promoting effect of ethanolamine hydrochloride.

The experiment was performed in 3 series for each medium, and the average results are shown in FIG. 11. The values are shown as relative values to the ethanolamine hydrochloride non-addition group (0 μM). Ethanolamine hydrochloride was found to show a proliferation-promoting effect in a relatively wide concentration range.

Example 6. Influence of Oleic Acid

To a solution (25%, 40 ml) of human serum albumin (Nova Biologics) in saline was added phosphate buffer (pH 7.2, 40 ml). Furthermore, a suspension of activated carbon (5 g, manufactured by Wako Pure Chemical Industries, Ltd.) heated at 200° C. for 30 min in advance in phosphate buffer (20 ml) was added to 100 ml. After stirring at 4° C. for 3 hr, the mixture was centrifuged at 4° C., 11,900 rpm for 20 min. Sedimented activated carbon was removed by decantation, and the reaction mixture was filtered with a 0.22 μm syringe filter, whereby human serum albumin with fatty acid removal treatment was obtained. Then, oleic acid was added to the obtained human serum albumin with fatty acid removal treatment to prepare human serum-derived albumin having a fatty acid carried amount of 2.2, 6.5, 21.7 mg/g, and each albumin was added to the medium to a final concentration of 2.6 g/l (final concentration of oleic acid in the medium 20, 60, 200 μM, respectively). Ethanolamine (final concentration 30 μM) was added to each medium. Using each medium, the cells were cultured for one week, and the cell number after culture was confirmed to study the influence of oleic acid. 13,000 viable cells per well were used for single cell-seeding. As a basal lamina matrix, a fragment containing the active domain of laminin 511, which was purchased from Osaka University, was applied at 4.8 μg/well. Y-27632 was added (final concentration 10 μM, Nacalai Tesque: 08945-84) to the medium used for seeding. The cells were cultured in a medium free of Y-27632 from the following day. The number of viable cells was measured by Cell Viability autoanalyzer ViCELL™ XR (BECKMAN COULTER).

Figure 12:
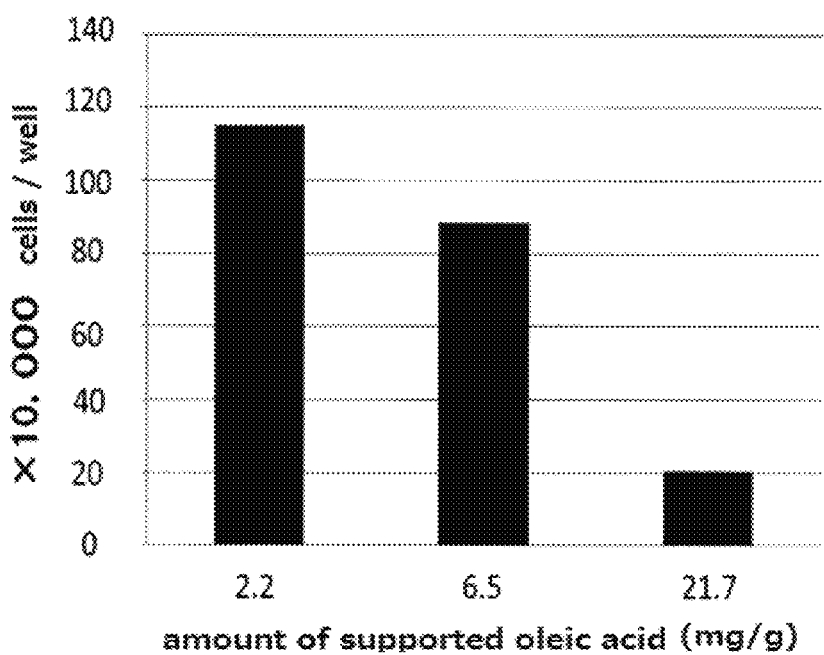
FIG. 12 shows a cell proliferation suppressive effect along with an increase in the amount of oleic acid carried by albumin.

The results of culture using each medium are shown in FIG. 12. It was found that cell proliferation was suppressed along with an increasing amount of oleic acid carried by albumin.

INDUSTRIAL APPLICABILITY

According to the present invention, pluripotent stem cells can be stably and efficiently proliferated, and can be stably proliferated for a long term while maintaining an undifferentiated state even in serum-free, feeder-free and single cell-seeding culture, and therefore, it is useful in the field of regenerative medicine and the like.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A culture medium suitable for proliferation of a pluripotent stem cell while maintaining an undifferentiated state, the medium comprising:
   a basal medium selected from the group consisting of DMEM, EMEM, IDMM (Iscove's Modified Dulbecco's Medium), GMEM (Glasgow's MEM), RPMI-1640, α-MEM, Ham's Medium F-12, Ham's Medium F-10, Ham's Medium F12K, Medium 199, ATCC-CRCM30, DM-160, DM-201, BME, Fischer, McCoy's 5A, Leibovitz's L-15, RITC80-7, MCDB105, MCDB107, MCDB131, MCDB153, MCDB201, NCTC109, NCTC135, Waymouth's MB752/1, CMRL- 1066, Williams' medium E, Brinster's BMOC-3 Medium, E8 medium, and mixtures thereof,
an albumin carrying not more than 2.2 mg/g of a fatty acid; and
at least one member selected from the group consisting of ethanolamine, an ethanolamine analog, and a pharmaceutically acceptable salt thereof,
wherein the medium is substantially free of β-mercaptoethanol or contains β-mercaptoethanol in a concentration of not more than 9 µM,
wherein a concentration of the at least one member in the medium is 11 µM to 200 µM, based on a volume of the medium,
wherein a concentration of albumin in the medium is 0.1 g/l-20 g/l, and
wherein a molar ratio of the albumin and the at least one member in the medium is 1:0.15-3.8.

2. The culture medium according to claim 1, which is substantially free of β-mercaptoethanol.

3. A culture method for proliferation of a pluripotent stem cell while maintaining an undifferentiated state, comprising:
cultivating the pluripotent stem cell in a medium which comprises an albumin carrying not more than 9 mg/g of a fatty acid, at least one member selected from the group consisting of ethanolamine, an ethanolamine analog, and a pharmaceutically acceptable salt thereof,
wherein the medium is substantially free of β-mercaptoethanol or contains β-mercaptoethanol in a concentration of not more than 9 µM,
wherein a concentration of the at least one member in the medium is 11 µM to 200 µM, based on a volume of the medium,
wherein a concentration of the albumin in the medium is 0.1 g/l-20 g/l, and
wherein a molar ratio of the albumin and the at least one member in the medium is 1:0.15-3.8.

4. The method according to claim 3, wherein the medium is substantially free of β-mercaptoethanol.

5. The method according to claim 3, wherein the amount of fatty acid carried by the albumin in the medium is not more than 2.2 mg/g, based on the weight of the albumin.

6. The method according to claim 3, wherein the cultivating is performed in the absence of a feeder cell.

7. The method according to claim 6, wherein the cultivating is performed by using an extracellular matrix or an active fragment thereof, or an artificial product mimicking the function thereof.

8. The method according to claim 3, wherein the cultivating is performed by single cell-seeding.

9. The method according to claim 3, wherein the pluripotent stem cell is an embryonic stem cell (ES cell) or an induced pluripotent stem cell (iPS cell).

10. A preservation stabilizing method for a medium suitable for proliferation of a pluripotent stem cell, comprising:
adding to a medium, an albumin carrying not more than 2.2 mg/g of a fatty acid, at least one member selected from the group consisting of ethanolamine, an ethanolamine analog, and a pharmaceutically acceptable salt thereof, and a sulfated saccharide and/or a pharmaceutically acceptable salt thereof, such that a concentration of the at least one member in the medium is 11 µM to 200 µM, based on a volume of the medium, that a concentration of the albumin in the medium is 0.1 g/l-20 g/l, and that a molar ratio of the albumin and the at least one member in the medium is 1:0.15-3.8.

11. The method according to claim 10, wherein the medium after the adding is substantially free of β-mercaptoethanol.

* * * * *